United States Patent
Khetani et al.

(10) Patent No.: US 10,682,336 B2
(45) Date of Patent: Jun. 16, 2020

(54) PDE4 MODULATORS FOR TREATING AND PREVENTING IMMUNE RECONSTITUTION INFLAMMATORY SYNDROME (IRIS)

(71) Applicant: Celgene Corporation, Summit, NJ (US)

(72) Inventors: Vikram Khetani, Short Hills, NJ (US); Jerome Zeldis, Princeton, NJ (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/769,713

(22) PCT Filed: Oct. 20, 2016

(86) PCT No.: PCT/US2016/057820
§ 371 (c)(1),
(2) Date: Apr. 19, 2018

(87) PCT Pub. No.: WO2017/070291
PCT Pub. Date: Apr. 27, 2017

(65) Prior Publication Data
US 2018/0318257 A1 Nov. 8, 2018

Related U.S. Application Data

(60) Provisional application No. 62/244,586, filed on Oct. 21, 2015.

(51) Int. Cl.
| *A61P 31/22* | (2006.01) |
| *A61P 31/14* | (2006.01) |
| *A61P 31/06* | (2006.01) |
| *A61P 31/10* | (2006.01) |
| *C07K 14/81* | (2006.01) |
| *A61K 31/4035* | (2006.01) |
| *A61K 45/06* | (2006.01) |

(52) U.S. Cl.
CPC .......... *A61K 31/4035* (2013.01); *A61P 31/06* (2018.01); *A61P 31/10* (2018.01); *A61P 31/14* (2018.01); *A61P 31/22* (2018.01); *C07K 14/81* (2013.01); *A61K 45/06* (2013.01); *A61K 2300/00* (2013.01)

(58) Field of Classification Search
CPC ............ A61K 31/4035; A61K 2300/00; A61K 45/06; A61P 31/22; A61P 31/14; A61P 31/06; A61P 31/10; C07K 14/81
USPC ....................................................... 514/417
See application file for complete search history.

(56) References Cited

U.S. PATENT DOCUMENTS

| 5,463,063 A | 10/1995 | Muller |
| 5,605,914 A | 2/1997 | Muller |
| 5,658,940 A | 8/1997 | Muller et al. |
| 5,698,579 A | 12/1997 | Muller et al. |
| 5,703,098 A | 12/1997 | Muller et al. |
| 5,728,844 A | 3/1998 | Muller et al. |
| 5,728,845 A | 3/1998 | Muller et al. |
| 5,736,570 A | 4/1998 | Muller et al. |
| 5,801,195 A | 9/1998 | Muller et al. |
| 5,877,200 A | 3/1999 | Muller |
| 5,929,117 A | 7/1999 | Muller et al. |
| 5,968,945 A | 10/1999 | Muller et al. |
| 6,011,050 A | 1/2000 | Muller et al. |
| 6,020,358 A | 2/2000 | Muller et al. |
| 6,046,221 A | 4/2000 | Muller et al. |
| 6,075,041 A | 6/2000 | Muller |
| 6,130,226 A | 10/2000 | Muller et al. |
| 6,180,644 B1 | 1/2001 | Muller et al. |
| 6,200,987 B1 | 3/2001 | Muller |
| 6,214,857 B1 | 4/2001 | Muller et al. |
| 6,262,101 B1 | 7/2001 | Muller et al. |
| 6,284,780 B1 | 9/2001 | Muller et al. |
| 6,326,388 B1 | 12/2001 | Man et al. |
| 6,429,221 B1 | 8/2002 | Muller et al. |
| 6,479,554 B2 | 11/2002 | Muller et al. |
| 6,518,281 B2 | 2/2003 | Muller et al. |
| 6,667,316 B1 | 12/2003 | Man et al. |
| 6,699,899 B1 | 3/2004 | Man et al. |
| 6,911,464 B2 | 6/2005 | Man et al. |
| 6,962,940 B2 | 11/2005 | Muller et al. |
| 7,034,052 B2 | 4/2006 | Man et al. |
| 7,173,058 B2 | 2/2007 | Muller et al. |
| 7,244,759 B2 | 7/2007 | Muller et al. |
| 7,312,241 B2 | 12/2007 | Muller et al. |
| 7,893,101 B2 | 2/2011 | Muller et al. |
| 8,289,280 B2 | 10/2012 | Ansari et al. |
| 2004/0167199 A1 | 8/2004 | Muller et al. |
| 2006/0025457 A1 | 2/2006 | Muller et al. |

(Continued)

FOREIGN PATENT DOCUMENTS

| EP | 2818164 A1 | 12/2014 |
| WO | WO 1995/001348 A2 | 12/1995 |

(Continued)

OTHER PUBLICATIONS

Schett et al Therapeutic Advances in Musculoskeletal Disease, 2010, 271-278 (Year: 2010).*
Boulougouta et al Open Forum Infect Dis, 2019 6(6), 1-8 (Year: 2019).*
Grivennikov et al., "Immunity, inflammation, and cancer," *Cell*, 140:883-899 (2010).
Sharma et al., "HIV & immune reconstitution inflammatory syndrome (IRIS)," *Indian J.Med. Res.*, 134:866-877 (2011).
Strashun et al., "Gated blood pool scintigraphic monitoring of doxorubicin cardiomyopathy: comparison of camera and computerized probe results in 101 patients," *J. Am. Coll. Cardiol.*, 8:1082-1087 (1986).

(Continued)

*Primary Examiner* — Yevgeny Valenrod
(74) *Attorney, Agent, or Firm* — Marshall, Gerstein & Borun LLP

(57) ABSTRACT

Methods of treating immune reconstitution inflammatory syndrome (IRIS) in immunodeficient patients, including HIV patients, using PDE4 modulators are described.

23 Claims, No Drawings

(56) References Cited

U.S. PATENT DOCUMENTS

| | | |
|---|---|---|
| 2009/0192227 A1 | 7/2009 | Tirouvanziam et al. |
| 2010/0168475 A1 | 7/2010 | Saindane et al. |

FOREIGN PATENT DOCUMENTS

| | | |
|---|---|---|
| WO | WO 1997/008143 A1 | 3/1997 |
| WO | WO 1997/023457 A1 | 7/1997 |
| WO | WO 1999/006041 A1 | 2/1999 |
| WO | WO 2001/034606 A1 | 5/2001 |
| WO | WO 2001/045702 A1 | 6/2001 |
| WO | WO 2001/090076 A1 | 11/2001 |
| WO | WO 2003/080048 A1 | 10/2003 |
| WO | WO 2003/080049 A1 | 10/2003 |

OTHER PUBLICATIONS

Subbian et al., "Phosphodiesterase-4 inhibition combined with isoniazid treatment of rabbits with pulmonary tuberculosis reduces macrophage activation and lung pathology," *Am. J. Pathol*, 179:289-301 (2011).

Wilen et al., "Strategies in optical resolutions," *Tetrahedron*, 33:2725-2736 (1977).

\* cited by examiner

PDE4 MODULATORS FOR TREATING AND PREVENTING IMMUNE RECONSTITUTION INFLAMMATORY SYNDROME (IRIS)

CROSS REFERENCE TO RELATED APPLICATIONS

This application is a National Stage of International Application No. PCT/US2016/057820, filed Oct. 20, 2016; which claims the benefit of U.S. Provisional Application No. 62/244,586, filed Oct. 21, 2015; the disclosure of each of which is incorporated by reference in its entirety.

1. FIELD

Provided herein are compositions and methods for the treatment of IRIS by administering to a patient in need thereof an effective amount of a PDE4 modulator described herein.

2. BACKGROUND

One goal of antiretroviral therapy (ART) in immunocompromised HIV-infected individuals is immune reconstitution. Since its introduction, ART has led to declines in AIDS-associated morbidity and mortality. These benefits, in part, arise from increases in CD4+ cell counts and decreases in plasma HIV viral titers. However, following initiation and withdrawal of ART, opportunistic infections (OIs) and other HIV-related events can, and often do, still occur. These events can, in certain instances, create a cytokine storm of varying severity. Thus, the resulting increase in immune function can cause an exaggerated response to a disease or other pathogen leading to immune reconstitution inflammatory syndrome (IRIS). IRIS can occur at any CD4+ count and at any time during the administration of ART, though it usually presents within the first 4 to 8 weeks after (re) initiation of ARV therapy.

There is currently no standard of care for treating IRIS. Thus, the onset of IRIS in an immunodeficient individual (such as HIV patients) can rapidly become severe resulting in increased morbidity and mortality of HIV patients. What is more, there is no determinant factor whether an individual will develop IRIS, and if they do how severe the IRIS will be. Thus, there is a need in the art for therapies to prevent, treat, and modulate IRIS in immunodeficient patients, particularly in HIV patients undergoing ART. Solutions to this and other problems in the art are provided herein.

3. SUMMARY

Provided herein, inter alia, are methods of treating or managing immunodeficient patients that develop immune reconstitution inflammatory syndrome (IRIS). Further provided herein are methods of preventing IRIS in an immunodeficient patient who is considered at risk of developing IRIS.

In one aspect is a method of treating, preventing, or managing IRIS in a patient in need thereof by administering to the patient an effective amount of a PDE4 modulator described herein.

In another aspect is a method of treating or managing IRIS in a patient in need thereof by administering to the patient an effective amount of a PDE4 modulator described herein.

In another aspect is a method of treating IRIS in a patient in need thereof by administering to the patient an effective amount of a PDE4 modulator described herein.

In still another aspect is a method for preventing the onset of IRIS in a patient at risk of developing IRIS by administering to the patient an effective amount of a PDE4 modulator. In one embodiment, a PDE4 modulator described herein is administered prior to a therapy that can cause IRIS.

In yet another aspect is a method for preventing the onset of IRIS in a HIV patient at risk of developing IRIS by administering to the patient an effective amount of a PDE4 modulator described herein before administration of ART.

In still yet another aspect is a method of treating or managing IRIS in a HIV patient by administering to the patient an effective amount of a PDE4 modulator described herein. In one embodiment, the PDE4 modulator is administered after (re)initiation of ART.

In still yet another aspect is a method of treating IRIS in a HIV patient by administering to the patient an effective amount of a PDE4 modulator described herein. In one embodiment, the PDE4 modulator is administered after (re)initiation of ART.

In another aspect is a method of preventing the onset of IRIS in a HIV patient at risk of developing IRIS by administering to the patient an effective amount of a PDE4 modulator described herein before withdrawal of ART.

In yet another aspect is a method of treating or managing IRIS in a HIV patient, wherein the IRIS occurs after withdrawal of ART, by administering to the patient an effective amount of a PDE4 modulator described herein.

In yet another aspect is a method of treating IRIS in a HIV patient, wherein the IRIS occurs after withdrawal of ART, by administering to the patient an effective amount of a PDE4 modulator described herein.

In one embodiment, the PDE4 modulator is

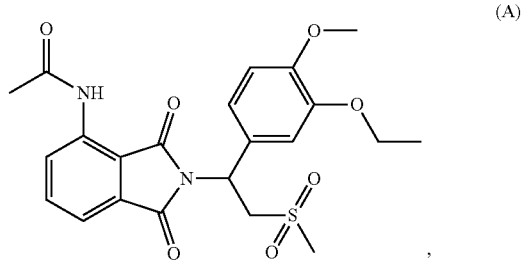
(A)

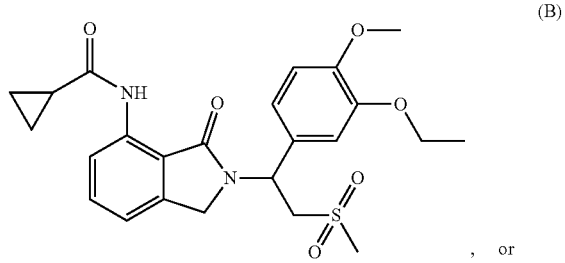
(B)
, or

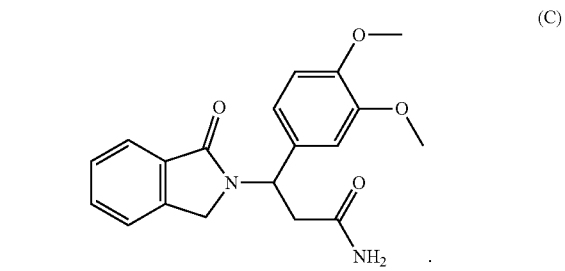
(C)

In one embodiment the PDE4 modulator is an enantiomer of compounds (A), (B), or (C). In one embodiment the PDE4 modulator is a mixture of enantiomers of either compound (A), (B) or (C). In a further embodiment, the PDE4 modulator is a pharmaceutically acceptable salt, solvate, hydrate, clathrate, or prodrug of compounds (A), (B) or (C). In one embodiment the PDE4 modulator is a mixture of (A) and (B), (A) and (C), (B) and (C) or (A), (B), and (C) or enantiomers thereof.

In one embodiment, the PDE4 modulator is

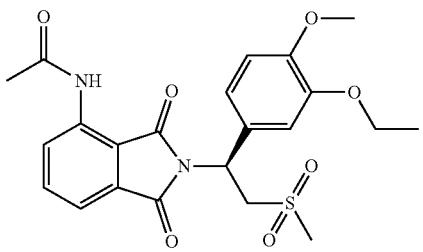 [SMILES: CCOc1cc([C@@H](CS(C)(=O)=O)N2C(=O)c3cccc(NC(C)=O)c3C2=O)ccc1OC]

or a pharmaceutically acceptable salt, solvate, hydrate, clathrate, or prodrug thereof.

In one embodiment, the PDE4 modulator is

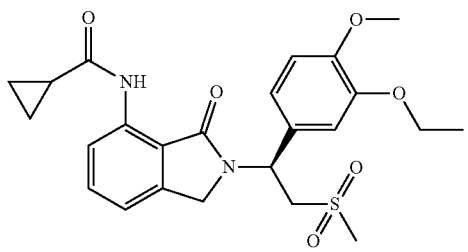 [SMILES: CCOc1cc([C@@H](CS(C)(=O)=O)N2Cc3cccc(NC(=O)C4CC4)c3C2=O)ccc1OC]

or a pharmaceutically acceptable salt, solvate, hydrate, clathrate, or prodrug thereof.

In one embodiment, the PDE4 modulator is

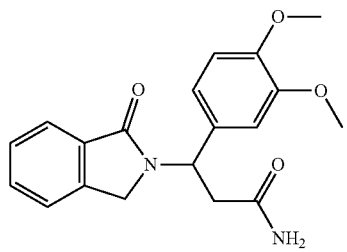 [SMILES: COc1ccc(C(CC(N)=O)N2Cc3ccccc3C2=O)cc1OC]

or a pharmaceutically acceptable salt, solvate, hydrate, clathrate, or prodrug thereof.

In one embodiment, the PDE4 modulator is administered orally.

In one embodiment, the PDE4 modulator is administered in a tablet, capsule, or satchet form.

In one embodiment, the PDE4 modulator is a component of a pharmaceutical composition.

In one embodiment, the PDE4 modulator is co-administered with one or more second active agents described herein.

In one embodiment, the PDE4 modulator is co-administered with a non-steroidal anti-inflammatory drug (NSAID) or a corticosteroid.

In one embodiment, the PDE4 modulator inhibits production or signaling of one or more cytokines.

In one embodiment, the PDE4 modulator inhibits production or signaling of one or more cytokines selected from one or more of TNF-α, IL-12, MIP-1α, MCP-1, IP-10, IFN-γ, MIG, GM-CSF, IL-1β, RANTES, and IL-8.

In one embodiment, the patient is a patient at risk of developing IRIS.

In one embodiment, the patient at risk of developing IRIS is an HIV patient.

In one embodiment, the patient presents or has already developed IRIS.

In one embodiment, the IRIS develops after initiation or re-initiation of ART to a HIV patient described herein.

In one embodiment, the IRIS develops after withdrawal of ART to a HIV patient described herein.

In one embodiment, the patient is an HIV patient as described herein.

In one embodiment, the IRIS is characterized by or results from an opportunistic bacterial infection.

In one embodiment, the IRIS is characterized by or results from an opportunistic parasitic infection.

In one embodiment, the opportunistic parasitic infection is a *Leishmania donovani* (e.g., Kala Azar) or *Plasmodium falcipaum* (e.g., malaria) infection.

In one embodiment, the IRIS is characterized by or caused by cytomegalovirus (CMV), CMV retinitis, *Crytoccocal meningitis, croyptococcosis*, eosinophilic folliculitis, hepatitis B, hepatitis C, herpes virus, herpes simplex virus (HSV), varicella zoster virus (shingles), human pampillomavirus (HPV), karposi sarcoma (HHV8), *Mycobacterium avium* complex (MAC), *Pneumocystis jiroveci* pneumonia (PCP), progressive multifocal leukoencephalopathy (PML), or *Mycobacterium tuberculosis* (TB) infection.

In one embodiment, the administration of a PDE4 modulator described herein occurs before administration of ART to a HIV patient described herein.

In one embodiment, the administration of a PDE4 modulator described herein occurs after initiation or re-initiation of ART to a HIV patient described herein.

In one embodiment, the administration of a PDE4 modulator described herein occurs before withdrawal of ART to a HIV patient described herein.

In one embodiment, the ART includes administration of one or more nucleoside reverse transcriptase inhibitors (NRTIs), non-nucleoside reverse transcriptase inhibitors (NNRTIs), protease inhibitors (PIs), fusion inhibitors (FIs), or chemokine receptor antagonists (CCR5 antagonists).

In one embodiment, the patient has a decreased CD4+ count before administration of ART compared to a non-immunodeficient subject.

In one embodiment, the patient has an increase in CD4+ count after administration of ART compared to before administration of ART.

In one embodiment, the patient has a decreased HIV titer as compared to a HIV titer taken before administration of ART.

4. DETAILED DESCRIPTION

4.1 Definitions

All patents, applications, published applications and other publications are incorporated by reference in their entirety. The abbreviations used herein have their conventional meaning within the chemical and biological arts. The chemical structures and formulae set forth herein are constructed according to the standard rules of chemical valency known in the chemical arts. In the event that there is a plurality of definitions for a term herein, those in this section prevail unless stated otherwise. Headings used herein are for organizational purposes only and in no way limit the invention described herein.

As used herein and unless otherwise indicated, the term "PDE4 modulator" encompasses small molecule drugs, e.g., small organic molecules which are not peptides, proteins, nucleic acids, oligosaccharides or other macromolecules. Certain compounds inhibit TNF-α production. Compounds can also inhibit other cytokines such as, for example, MIP-1α, MCP-1, IP-10, IFN-γ, MIG, GM-CSF, RANTES, and IL-8. Compounds may also have an inhibitory effect on LPS induced IL1β and IL12. More preferably, the compounds provided herein are potent PDE4 inhibitors.

As used herein, the term "Compound A" refers to N-(2-(1-(3-ethoxy-4-methoxyphenyl)-2-(methylsulfonyl)ethyl)-1,3-dioxoisoindolin-4-yl)acetamide, also known as 2-[1-(3-ethoxy-4-methoxyphenyl)-2-methylsulfonylethyl]-4-acetylaminoisoindoline-1,3-dione, which has the following structure:

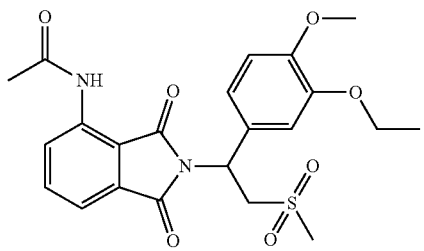

(A)

Compound A also refers to any crystal form or polymorph of N-(2-(1-(3-ethoxy-4-methoxyphenyl)-2-(methylsulfonyl)ethyl)-1,3-dioxoisoindolin-4-yl)acetamide.

As used herein, the term "Compound A1" refers to an enantiomerically pure form of 2-[1-(3-ethoxy-4-methoxyphenyl)-2-methylsulfonylethyl]-4-acetylaminoisoindoline-1,3-dione, also known as apremilast, and which when dissolved in methanol rotates plane polarized light in the (+) direction. Without being limited by theory, Compound A1 is believed to be (S)—N-(2-(1-(3-ethoxy-4-methoxyphenyl)-2-(methylsulfonyl)ethyl)-1,3-dioxoisoindolin-4-yl)acetamide, which has the following structure:

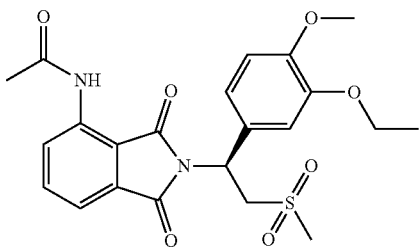

(A1)

Compound A1 also refers to any crystal form or polymorph of (S)—N-(2-(1-(3-ethoxy-4-methoxyphenyl)-2-(methylsulfonyl)ethyl)-1,3-dioxoisoindolin-4-yl)acetamide. Examples of crystal form or polymorph of Compound A1 include, but are not limited to, those disclosed in U.S. Pat. No. 7,893,101.

As used herein, the term "Compound A2" refers to an enantiomerically pure form of 2-[1-(3-ethoxy-4-methoxyphenyl)-2-methylsulfonylethyl]-4-acetylaminoisoindoline-1,3-dione, which when dissolved in methanol rotates plane polarized light in the (−) direction. Without being limited by theory, Compound A2 is believed to be (R)—N-(2-(1-(3-ethoxy-4-methoxyphenyl)-2-(methylsulfonyl)ethyl)-1,3-dioxoisoindolin-4-yl)acetamide. Compound A2 also refers to any crystal form or polymorph of (R)—N-(2-(1-(3-ethoxy-4-methoxy-phenyl)-2-(methylsulfonyl)ethyl)-1,3-dioxoisoindolin-4-yl)acetamide.

As used herein, the term "Compound B" refers to N-(2-(1-(3-ethoxy-4-methoxyphenyl)-2-(methylsulfonyl)ethyl)-3-oxoisoindolin-4-yl)cyclopropanecarboxamide, also known as cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide, which has the following structure:

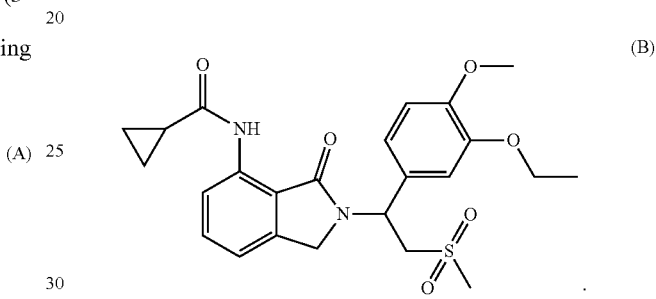

(B)

Compound B also refers to any crystal form or polymorph of N-(2-(1-(3-ethoxy-4-methoxyphenyl)-2-(methylsulfonyl)ethyl)-3-oxoisoindolin-4-yl)cyclopropanecarboxamide.

As used herein, the term "Compound B1" refers to enantiomerically pure cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide. Without being limited by theory, Compound B1 is believed to be (S)—N-(2-(1-(3-ethoxy-4-methoxyphenyl)-2-(methylsulfonyl)ethyl)-3-oxoisoindolin-4-yl)cyclopropanecarboxamide, which has the following structure:

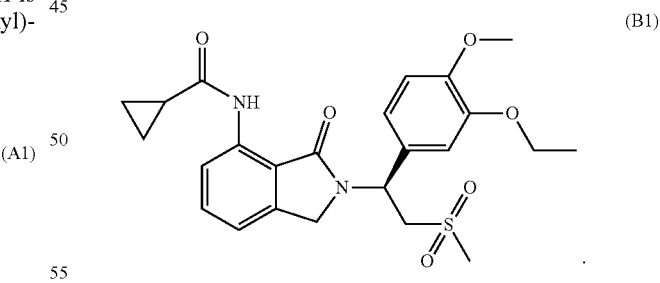

(B1)

Compound B1 also refers to any crystal form or polymorph of (S)—N-(2-(1-(3-ethoxy-4-methoxyphenyl)-2-(methylsulfonyl)ethyl)-3-oxoisoindolin-4-yl)cyclopropanecarboxamide.

As used herein, the term "Compound B2" refers to enantiomerically pure cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide. Without being limited by theory, Compound B2 is believed to be (R)—N-(2-(1-(3-ethoxy-4-methoxyphenyl)-2-(methylsulfonyl)ethyl)-3-oxoisoindolin-4-yl)cyclopropanecarboxamide.

Compound B2 also refers to any crystal form or polymorph of (R)—N-(2-(1-(3-ethoxy-4-methoxyphenyl)-2-(methylsulfonyl)ethyl)-3-oxoisoindolin-4-yl)cyclopropanecarboxamide.

As used herein, the term "Compound C" refers to 3-(3,4-dimethoxyphenyl)-3-(1-oxoisoindolin-2-yl)propanamide, also known as 3-(3,4-dimethoxy-phenyl)-3-(1-oxo-1,3-dihydro-isoindol-2-yl)-propionamide, which has the following chemical structure:

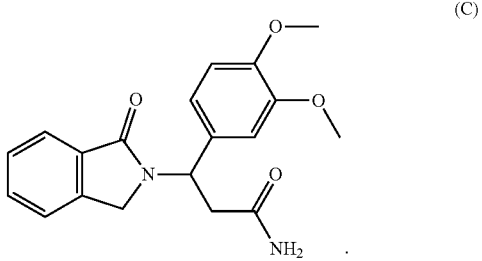 [SMILES: COc1ccc(C(CC(N)=O)N2Cc3ccccc3C2=O)cc1OC]

(C)

Compound C also refers to any crystal form or polymorph of 3-(3,4-dimethoxyphenyl)-3-(1-oxoisoindolin-2-yl)propanamide.

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide an active form of a compound. Examples of prodrugs include, but are not limited to, derivatives and metabolites of (+)-2-[1-(3-ethoxy-4-methoxyphenyl)-2-methylsulfonylethyl]-4-acetylaminoisoindoline-1,3-dione that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 90%, 95%, 98% or 99% of one stereoisomer, and 20%, 10%, 5%, 2%, 1% or less of the counter stereoisomer. "Substantially free of its (−) enantiomer" is encompassed by the term stereomerically pure or enantiomerically pure.

As used herein, and unless otherwise indicated, the term "stereomerically enriched" or "enantiomerically enriched" encompasses racemic mixtures as well as other mixtures of stereoisomers of compounds provided herein (e.g., R/S=30/70, 35/65, 40/60, 45/55, 55/45, 60/40, 65/35 and 70/30).

As used herein, the term "subject" means an animal, including mammals, (e.g., cow, horse, sheep, pig, chicken, turkey, quail, cat, dog, mouse, rat, rabbit, guinea pig, etc.). In certain embodiments, the subject is a mammal such as a non-primate or a primate (e.g., monkey and human). In certain embodiments, the subject is a human.

As used herein the term "patient" refers to a human. In certain embodiments, the patient is a fetus, embryo, infant, child, adolescent or adult. Patients described herein can also be referred to with respect to a disease indication (e.g., HIV patient refers to a human with HIV). In one embodiment, the subject is a human with IRIS. In another embodiment, the subject is a human at risk of developing IRIS.

As used herein, the terms "immune reconstitution inflammatory disease" and "IRIS" are used interchangeably herein and refer to inflammatory disorders associated with paradoxical worsening of preexisting or opportunistic infectious processes following the initiation of antiretroviral therapy ((ART), such as highly active antiretroviral therapy (HAART)) in HIV-infected individuals. As provided herein, opportunistic or preexisting infections in individuals with IRIS may have been previously diagnosed or treated, or such infections may be subclinical and later unmasked by the host's regained capacity to mount an inflammatory response.

As used herein, an "opportunistic" disease or infection is a disease or infection that occurs in an immunodeficient (e.g., HIV) patient. In certain embodiments, an opportunistic infection described herein occurs only because of a weakened immune system of the patient.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

As used herein, unless otherwise specified, the term "preventing" refers to the treatment with or administration of a compound provided herein, with or without other additional active compound, prior to the onset of symptoms, particularly to patients at risk of or who have already developed IRIS. The term "prevention" includes the inhibition or reduction of a symptom of IRIS. The term "prevention" may be interchangeably used with the term "prophylactic treatment."

As used herein, and unless otherwise specified, a "prophylactically effective amount" of a compound is an amount sufficient to inhibit or reduce a symptom of IRIS. A prophylactically effective amount of a compound means an amount of therapeutic agent, alone or in combination with other agents, which provides a prophylactic benefit in the inhibition or reduction of a symptom of IRIS. The term "prophylactically effective amount" can encompass an amount that improves overall prophylaxis or enhances the prophylactic efficacy of another prophylactic agent.

The term "effective amount" as used herein refers to the amount of a therapy (e.g., a composition provided herein) which is sufficient to reduce and/or ameliorate the severity and/or duration of a given disease, disorder or condition and/or a symptom related thereto. This term also encompasses an amount necessary for the reduction or amelioration of the advancement or progression of a given disease, disorder or condition, reduction or amelioration of the recurrence, development or onset of a given disease, disorder or condition, and/or to improve or enhance the prophylactic or therapeutic effect(s) of another therapy. In some embodiments, "effective amount" as used herein also refers to the amount of therapy provided herein to achieve a specified result.

As used herein, and unless otherwise specified, the term "therapeutically effective amount" of a compound is an amount sufficient to provide a therapeutic benefit in the treatment or management IRIS, or to delay or minimize one or more symptoms associated with IRIS. A therapeutically effective amount of a compound means an amount of therapeutic agent, alone or in combination with other therapies, which provides a therapeutic benefit in the treatment or management of IRIS. The term "therapeutically effective amount" can encompass an amount that improves overall therapy, reduces or avoids symptoms or causes of IRIS, or enhances the therapeutic efficacy of another therapeutic agent.

As used herein, the term "therapy" refers to any protocol, method and/or agent that can be used in the prevention, management, treatment and/or amelioration of a given disease, disorder or condition. In certain embodiments, the terms "therapies" and "therapy" refer to a drug therapy, biological therapy, supportive therapy, and/or other therapies useful in the prevention, management, treatment and/or amelioration of a given disease, disorder or condition known to one of skill in the art such as medical personnel. "Withdrawal" of a therapy as used herein refers to both a lessening of the amount of medicine administered to a patient in need thereof and to completion of the therapy (e.g., ART is no longer administered to the patient).

The term "pharmaceutically acceptable" as used herein means being approved by a regulatory agency of the Federal or state government, or listed in the U.S. Pharmacopeia, European Pharmacopeia or other generally recognized Pharmacopeia for use in animals, and more particularly in humans.

As used herein the terms "antiretroviral therapy" and "ART," are used interchangeably and refer to a therapy that slows, hinders, inhibits, or otherwise controls HIV infection and progression of HIV infection. The terms "highly active antiretroviral therapy," and "HAART" are used interchangeably herein and refer to herein to combination therapies (e.g., multiple different drugs having different effects on HIV stages) that are administered to slow the rate of HIV progression. ART, as used herein, is inclusive of HAART. Such therapies are well known in the art and include different classes of drugs including, for example, nucleoside reverse transcriptase inhibitors (NRTIs), non-nucleoside reverse transcriptase inhibitors (NNRTIs), protease inhibitors (PIs), fusion inhibitors (FIs), integrase inhibitors, entry inhibitors, or chemokine receptor antagonists (CCR5 antagonists).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & S J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

4.2 PDE4 Modulators

PDE4 is one phosphodiesterase isoenzyme found in human myeloid and lymphoid lineage cells. The enzyme plays a crucial part in regulating cellular activity by degrading the ubiquitous second messenger cAMP and maintaining it at low intracellular levels. Without being limited by theory, inhibition of PDE4 activity results in increased cAMP levels leading to the modulation of LPS induced cytokines, including inhibition of, among other cytokines, TNF-α production in monocytes as well as in lymphocytes.

The compounds provided herein include racemic, stereomerically pure and stereomerically enriched PDE4 modulators, stereomerically and enantiomerically pure compounds that have selective cytokine inhibitory activities, and pharmaceutically acceptable salts, solvates, hydrates, stereoisomers, clathrates, and prodrugs thereof. Certain compounds provided herein are known PDE4 modulators of Celgene Corporation, NJ. Without being limited by a particular theory, compounds provided herein can inhibit PDE4 enzymatic activity, control angiogenesis or inhibit the production of certain cytokines including, but not limited to, TNF-α, INF-γ, IP-10, MIG, IL-1β, IL-12, IL-18, GM-CSF, and/or IL-6. Without being limited by a particular theory, compounds provided herein can, under certain circumstance, stimulate the production of certain other cytokines including IL-10, and also act as inhibitors of T cell activation, resulting in decreased production of cytokines such as, but not limited to, IL-2 and/or IFN-γ. In addition, compounds provided herein can inhibit the effects of NK cells.

In some embodiments, the PDE4 modulator is N-(2-(1-(3-ethoxy-4-methoxyphenyl)-2-(methylsulfonyl)ethyl)-1,3-dioxoisoindolin-4-yl)acetamide, or an enantiomer thereof, or a mixture of enantiomers thereof, or a pharmaceutically acceptable salt, solvate, hydrate, clathrate, or prodrug thereof. In one embodiment, the PDE4 modulator is N-(2-(1-(3-ethoxy-4-methoxyphenyl)-2-(methylsulfonyl)ethyl)-1,3-dioxoisoindolin-4-yl)acetamide (Compound A), or a pharmaceutically acceptable salt, solvate, hydrate, clathrate, or prodrug thereof. In one embodiment, the PDE4 modulator is N-(2-(1-(3-ethoxy-4-methoxyphenyl)-2-(methylsulfonyl)ethyl)-1,3-dioxoisoindolin-4-yl)acetamide (Compound A). In one embodiment, the PDE4 modulator is a pharmaceutically acceptable salt of N-(2-(1-(3-ethoxy-4-methoxyphenyl)-2-(methylsulfonyl)ethyl)-1,3-dioxoisoindolin-4-yl)acetamide (Compound A).

In one embodiment, the PDE4 modulator is (S)—N-(2-(1-(3-ethoxy-4-methoxyphenyl)-2-(methylsulfonyl)ethyl)-1,3-dioxoisoindolin-4-yl)acetamide (Compound A1), or a pharmaceutically acceptable salt, solvate, hydrate, clathrate, or prodrug thereof. In one embodiment, the PDE4 modulator is (S)—N-(2-(1-(3-ethoxy-4-methoxyphenyl)-2-(methylsulfonyl)ethyl)-1,3-dioxoisoindolin-4-yl)acetamide (Compound A1). In one embodiment, the PDE4 modulator is a pharmaceutically acceptable salt of (S)—N-(2-(1-(3-ethoxy-4-methoxyphenyl)-2-(methylsulfonyl)ethyl)-1,3-dioxoisoindolin-4-yl)acetamide (Compound A1).

In another embodiment, the PDE4 modulator is (R)—N-(2-(1-(3-ethoxy-4-methoxyphenyl)-2-(methylsulfonyl)ethyl)-1,3-dioxoisoindolin-4-yl)acetamide (Compound A2), or a pharmaceutically acceptable salt, solvate, hydrate, clathrate, or prodrug thereof. In another embodiment, the PDE4 modulator is (R)—N-(2-(1-(3-ethoxy-4-methoxyphenyl)-2-(methylsulfonyl)ethyl)-1,3-dioxoisoindolin-4-yl)acetamide (Compound A2). In another embodiment, the PDE4 modulator is a pharmaceutically acceptable salt of (R)—N-(2-(1-(3-ethoxy-4-methoxyphenyl)-2-(methylsulfonyl)ethyl)-1,3-dioxoisoindolin-4-yl)acetamide (Compound A2).

Compounds A, A1 and A2 can be prepared according to methods disclosed in U.S. Pat. No. 6,962,940, titled "(+)-2-[1-(3-Ethoxy-4-methoxyphenyl)-2-methylsulfonylethyl]-4-acetylaminoisoindoline-1,3-dione: Methods Of Using And Compositions Thereof," or U.S. Patent Publication No. 2010/0168475, each of which are incorporated herein by reference. Generally, racemic 2-[1-(3-ethoxy-4-methoxyphenyl)-2-methylsulfonylethyl]-4-acetylaminoisoindoline-1,3-dione can be readily prepared using the methods described in U.S. Pat. No. 6,020,358, which is incorporated herein by reference. The corresponding (+) and (−) enantiomers can be isolated from the racemic compound by techniques known in the art. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

In a specific method, the (+) enantiomer of 2-[1-(3-ethoxy-4-methoxyphenyl)-2-methylsulfonylethyl]-4-acetylaminoisoindoline-1,3-dione is synthesized from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3 ethoxy-4-methoxyphenyl)-1-(methylsulphonyl)-eth-2-ylamine include, but are not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, and N-acetyl-L-leucine. A specific chiral amino acid salt is (S)-2-(3-ethoxy-4-methoxyphenyl)-1-(methylsulphonyl)-eth-2-ylamine N-acetyl-L-leucine salt, which is resolved from 2-(3-ethoxy-4-methoxyphenyl)-1-(methylsulphonyl)-eth-2-ylamine and N-acetyl-L-leucine in methanol.

In some embodiments, the PDE4 modulator is N-(2-(1-(3-ethoxy-4-methoxyphenyl)-2-(methylsulfonyl)ethyl)-3-oxoisoindolin-4-yl)cyclopropanecarboxamide, or an enantiomer thereof, or a mixture of enantiomers thereof, or a pharmaceutically acceptable salt, solvate, hydrate, clathrate, or prodrug thereof. In one embodiment, the PDE4 modulator is N-(2-(1-(3-ethoxy-4-methoxyphenyl)-2-(methylsulfonyl)ethyl)-3-oxoisoindolin-4-yl)cyclopropanecarboxamide (Compound B), or a pharmaceutically acceptable salt, solvate, hydrate, clathrate, or prodrug thereof. In one embodiment, the PDE4 modulator is (S)—N-(2-(1-(3-ethoxy-4-methoxyphenyl)-2-(methylsulfonyl)ethyl)-3-oxoisoindolin-4-yl)cyclopropanecarboxamide (Compound B1), or a pharmaceutically acceptable salt, solvate, hydrate, clathrate, or prodrug thereof. In another embodiment, the PDE4 modulator is (R)—N-(2-(1-(3-ethoxy-4-methoxyphenyl)-2-(methylsulfonyl)ethyl)-3-oxoisoindolin-4-yl)cyclopropanecarboxamide (Compound B2), or a pharmaceutically acceptable salt, solvate, hydrate, clathrate, or prodrug thereof.

In some embodiments, the PDE4 modulator is 3-(3,4-dimethoxy-phenyl)-3-(1-oxo-1,3-dihydro-isoindol-2-yl)-propionamide, or an enantiomer thereof, or a mixture of enantiomers thereof, or a pharmaceutically acceptable salt, solvate, hydrate, clathrate, or prodrug thereof. In one embodiment, the PDE4 modulator is 3-(3,4-dimethoxy-phenyl)-3-(1-oxo-1,3-dihydro-isoindol-2-yl)-propionamide (Compound C), or a pharmaceutically acceptable salt, solvate, hydrate, clathrate, or prodrug thereof. In one embodiment, the PDE4 modulator is 3-(3,4-dimethoxy-phenyl)-3-(1-oxo-1,3-dihydro-isoindol-2-yl)-propionamide (Compound C). In one embodiment, the PDE4 modulator is a pharmaceutically acceptable salt of 3-(3,4-dimethoxyphenyl)-3-(1-oxo-1,3-dihydro-isoindol-2-yl)-propionamide (Compound C).

In one embodiment the PDE4 modulator is a mixture of (A) and (B), (A) and (C), (B) and (C) or (A), (B), and (C) or enantiomers thereof.

Examples of PDE4 modulators provided herein include, but are not limited to, the cyclic imides disclosed in U.S. Pat. Nos. 5,605,914 and 5,463,063; the cycloalkyl amides and cycloalkyl nitriles of U.S. Pat. Nos. 5,728,844, 5,728,845, 5,968,945, 6,180,644 and 6,518,281; the aryl amides (for example, an embodiment being N-benzoyl-3-amino-3-(3',4'-dimethoxyphenyl)-propanamide) of U.S. Pat. Nos. 5,801, 195, 5,736,570, 6,046,221 and 6,284,780; the imide/amide ethers and alcohols (for example, 3-phthalimido-3-(3',4'-dimethoxyphenyl)propan-1-ol) disclosed in U.S. Pat. No.

5,703,098; the succinimides and maleimides (for example methyl 3-(3',4',5'6'-petrahydrophthalimdo)-3-(3",4"-dimethoxyphenyl)propionate) disclosed in U.S. Pat. No. 5,658,940; imido and amido substituted alkanohydroxamic acids disclosed in U.S. Pat. No. 6,214,857 and WO 99/06041; substituted phenethylsulfones disclosed in U.S. Pat. Nos. 6,011,050 and 6,020,358; fluoroalkoxy-substituted 1,3-dihydro-isoindolyl compounds disclosed in U.S. Pat. No. 7,173,058; substituted imides (for example, 2-phthalimido-3-(3',4'-dimethoxyphenyl) propane) disclosed in U.S. Pat. No. 6,429,221; substituted 1,3,4-oxadiazoles (for example, 2-[1-(3-cyclopentyloxy-4-methoxyphenyl)-2-(1,3,4-oxadiazole-2-yl)ethyl]-5-methylisoindoline-1,3-dione) disclosed in U.S. Pat. No. 6,326,388; cyano and carboxy derivatives of substituted styrenes (for example, 3,3-bis-(3,4-dimethoxyphenyl) acrylonitrile) disclosed in U.S. Pat. Nos. 5,929,117, 6,130,226, 6,262,101 and 6,479,554; isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606 and U.S. Pat. No. 6,667,316, for example, cyclopropyl-N-{2-[1-(3-ethoxy-4-methoxyphenyl)-2-(methylsulfonyl)ethyl]-3-oxoisoindolin-4-yl}carboxamide, cyclopropyl-N-{2-[1(S)-(3-ethoxy-4-methoxyphenyl)-2-(methylsulfonyl)ethyl]-3-oxoisoindolin-4-yl}carboxamide, and cyclopropyl-N-{2-[1(R)-(3-ethoxy-4-methoxyphenyl)-2-(methylsulfonyl)ethyl]-3-oxoisoindolin-4-yl}carboxamide; and imido and amido substituted acylhydroxamic acids (for example, (3-(1,3-dioxoisoindoline-2-yl)-3-(3-ethoxy-4-methoxyphenyl) propanoylamino) propanoate disclosed in WO 01/45702 and U.S. Pat. No. 6,699,899. Other PDE4 modulators include diphenylethylene compounds disclosed in U.S. Pat. No. 7,312,241, the contents of which are incorporated by reference herein in their entirety. Other PDE4 modulators include isoindoline compounds disclosed in U.S. patent publication no. 2006/0025457A1, published Feb. 2, 2006 and U.S. Pat. No. 7,244,759. Other specific PDE4 modulators include 2-[1-(3-ethoxy-4-methoxyphenyl)-2-methylsulfonylethyl]-4-acetylaminoisoindoline-1,3-dione, and stereoisomers thereof. (+)-2-[1-(3-ethoxy-4-methoxyphenyl)-2-methylsulfonylethyl]-4-acetylaminoisoindoline-1,3-dione was disclosed in WO 03/080049. The entireties of each of the patents and patent applications identified herein are incorporated herein by reference.

Additional PDE4 modulators belong to a family of synthesized chemical compounds of which typical embodiments include 3-(1,3-dioxobenzo-[f]isoindol-2-yl)-3-(3-cyclopentyloxy-4-methoxyphenyl)propionamide and 3-(1,3-dioxo-4-azaisoindol-2-yl)-3-(3,4-dimethoxyphenyl)-propionamide.

Other PDE4 modulators belong to a class of non-polypeptide cyclic amides disclosed in U.S. Pat. Nos. 5,698,579, 5,877,200, 6,075,041 and 6,200,987, and WO 95/01348, each of which is incorporated herein by reference. Representative cyclic amides include compounds of the formula (X):

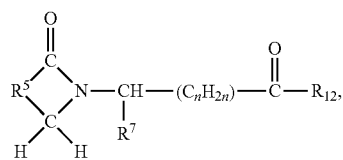

or a pharmaceutically acceptable salt, solvate, hydrate, clathrate, stereoisomer, or prodrug thereof, wherein the compounds of formula (X):

n has a value of 1, 2, or 3;

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, or halo;

$R^7$ is (i) phenyl or phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo; (ii) benzyl unsubstituted or substituted with 1 to 3 substituents selected from the group consisting of nitro, cyano, trifluoromethyl, carbothoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo; (iii) naphthyl; or (iv) benzyloxy;

$R^{12}$ is —OH, alkoxy of 1 to 12 carbon atoms, or

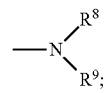

$R^8$ is hydrogen or alkyl of 1 to 10 carbon atoms; and
$R^9$ is hydrogen, alkyl of 1 to 10 carbon atoms, —COR$^{10}$, or —SO$_2$R$^{10}$,
$R^{10}$ is hydrogen, alkyl of 1 to 10 carbon atoms, or phenyl.

In some embodiments, the PDE4 modulator is selected from:
3-phenyl-2-(1-oxoisoindolin-2-yl)propionic acid;
3-phenyl-2-(1-oxoisoindolin-2-yl)propionamide;
3-phenyl-3-(1-oxoisoindolin-2-yl)propionic acid;
3-phenyl-3-(1-oxoisoindolin-2-yl)propionamide;
3-(4-methoxyphenyl)-3-(1-oxisoindolin-yl)propionic acid;
3-(4-methoxyphenyl)-3-(1-oxisoindolin-yl)propionamide;
3-(3,4-dimethoxyphenyl)-3-(1-oxisoindolin-2-yl)propionic acid;
3-(3,4-dimethoxy-phenyl)-3-(1-oxo-1,3-dihydroisoindol-2-yl)propionamide;
3-(3,4-dimethoxyphenyl)-3-(1-oxisoindolin-2-yl)propionamide;
3-(3,4-diethoxyphenyl)-3-(1-oxoisoindolin-yl)propionic acid;
methyl 3-(1-oxoisoindolin-2-yl)-3-(3-ethoxy-4-methoxyphenyl)propionate;
3-(1-oxoisoindolin-2-yl)-3-(3-ethoxy-4-methoxyphenyl) propionic acid;
3-(1-oxoisoindolin-2-yl)-3-(3-propoxy-4-methoxyphenyl) propionic acid;
3-(1-oxoisoindolin-2-yl)-3-(3-butoxy-4-methoxyphenyl) propionic acid;
3-(1-oxoisoindolin-2-yl)-3-(3-propoxy-4-methoxyphenyl) propionamide;
3-(1-oxoisoindolin-2-yl)-3-(3-butoxy-4-methoxyphenyl) propionamide;
methyl 3-(1-oxoisoindolin-2-yl)-3-(3-butoxy-4-methoxyphenyl)propionate; and
methyl 3-(1-oxoisoindolin-2-yl)-3-(3-propoxy-4-methoxyphenyl)propionate or a pharmaceutically acceptable salt, solvate, hydrate, clathrate, stereoisomer, or prodrug thereof.

Other representative cyclic amides include compounds of the formula (X1):

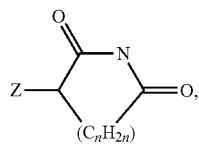

or a pharmaceutically acceptable salt, solvate, hydrate, clathrate, stereoisomer, or prodrug thereof,
wherein compounds of formula (X1):
Z is:

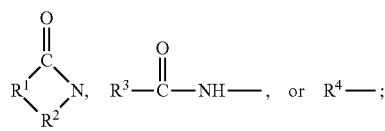

$R^1$ is the divalent residue of (i) 3,4-pyridine, (ii) pyrrolidine, (iii) imidizole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, wherein the divalent bonds of said residue are on vicinal ring carbon atoms;

$R^2$ is —CO— or —SO$_2$—;

$R^3$ is (i) phenyl substituted with 1 to 3 substituents each selected independently from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo; (ii) pyridyl; (iii) pyrrolyl; (iv) imidazolyl; (iv) naphthyl; (vi) thienyl; (vii) quinolyl; (viii) furyl; or (ix) indolyl;

$R^4$ is alanyl, arginyl, glycyl, phenylglycyl, histidyl, leucyl, isoleucyl, lysyl, methionyl, prolyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl; and n has a value of 1, 2, or 3.

Other representative cyclic amides include compounds of the formula (X2):

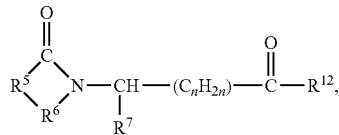

or a pharmaceutically acceptable salt, solvate, hydrate, clathrate, stereoisomer, or prodrug thereof, wherein compounds of formula (X2):

$R^5$ is (i) o-phenylene, unsubstituted or substituted with 1 to 4 substituents each selected independently from nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, or halo; or (ii) the divalent residue of pyridine, pyrrolidine, imidizole, naphthalene, or thiophene, wherein the divalent bonds are on vicinal ring carbon atoms;

$R^6$ is —CO—, —CH$_2$—, or —SO$_2$—;

$R^7$ is (i) hydrogen if $R^6$ is —SO$_2$—; (ii) straight, branched, or cyclic alkyl of 1 to 12 carbon atoms; (iii) pyridyl; (iv) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo; (v) alkyl of 1 to 10 carbon atoms; (vi) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo; (vii) naphthyl; (viii) benzyloxy; or (ix) imidazol-4-yl methyl;

$R^{12}$ is —OH, alkoxy of 1 to 12 carbon atoms, or

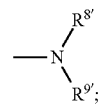

n has a value of 0, 1, 2, or 3;
$R^{8'}$ is hydrogen or alkyl of 1 to 10 carbon atoms; and
$R^{9'}$ is hydrogen, alkyl of 1 to 10 carbon atoms, —COR$^{10}$, or —SO$_2$R$^{10}$ in which R$^{10}$ is hydrogen, alkyl of 1 to 10 carbon atoms, or phenyl.

Other representative imides include compounds of the formula (X3):

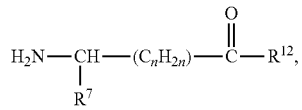

or a pharmaceutically acceptable salt, solvate, hydrate, clathrate, stereoisomer, or prodrug thereof, wherein compounds of formula (X3):

$R^7$ is (i) straight, branched, or cyclic alkyl of 1 to 12 carbon atoms; (ii) pyridyl; (iii) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo; (iv) benzyl unsubstituted or substituted with one to three substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 4 carbon atoms, or halo; (v) naphthyl; (vi) benzyloxy; or (vii) imidazol-4-ylmethyl;

$R^{12}$ is —OH, alkoxy of 1 to 12 carbon atoms, —O—CH$_2$-pyridyl, —O-benzyl or

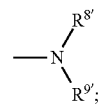

where n has a value of 0, 1, 2, or 3;

$R^{8'}$ is hydrogen or alkyl of 1 to 10 carbon atoms;

$R^{9'}$ is hydrogen, alkyl of 1 to 10 carbon atoms, —$CH_2$-pyridyl, benzyl, —$COR^{10}$, or —$SO_2R^{10}$; and $R^{10}$ is hydrogen, alkyl of 1 to 4 carbon atoms, or phenyl.

Other PDE4 modulators include the imido and amido substituted alkanohydroxamic acids disclosed in WO 99/06041 and U.S. Pat. No. 6,214,857, each of which is incorporated herein by reference. Examples of such compounds include, but are not limited to compounds of formula (X4):

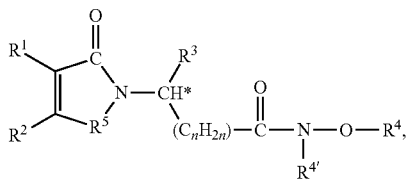

or a pharmaceutically acceptable salt, solvate, hydrate, clathrate, stereoisomer, or prodrug thereof, wherein compounds of formula (X4):

each of $R^1$ and $R^2$, when taken independently of each other, is hydrogen, lower alkyl; or $R^1$ and $R^2$, when taken together with the depicted carbon atoms to which each is bound, is o-phenylene, o-naphthylene, or cyclohexene-1,2-diyl, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo;

$R^3$ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$-$C_6$-cycloalkylidenemethyl, $C_3$-$C_{10}$-alkylidenemethyl, indanyloxy, and halo;

$R^4$ is hydrogen, alkyl of 1 to 6 carbon atoms, phenyl, or benzyl;

$R^{4'}$ is hydrogen or alkyl of 1 to 6 carbon atoms;

$R^5$ is —$CH_2$—, —$CH_2$—CO—, —$SO_2$—, —S—, or —NHCO—; and n has a value of 0, 1, or 2.

In some embodiments, the PDE4 modulator is the following compound, or a pharmaceutically acceptable salt, solvate, hydrate, clathrate, stereoisomer, or prodrug thereof:

3-(3-ethoxy-4-methoxyphenyl)-N-hydroxy-3-(1-oxoisoindolinyl)propionamide;

3-(3-ethoxy-4-methoxyphenyl)-N-methoxy-3-(1-oxoisoindolinyl)propionamide;

N-benzyloxy-3-(3-ethoxy-4-methoxyphenyl)-3-phthalimidopropionamide;

N-benzyloxy-3-(3-ethoxy-4-methoxyphenyl)-3-(3-nitrophthalimido)propionamide;

N-benzyloxy-3-(3-ethoxy-4-methoxyphenyl)-3-(1-oxoisoindolinyl)propionamide;

3-(3-ethoxy-4-methoxyphenyl)-N-hydroxy-3-phthalimidopropionamide;

N-hydroxy-3-(3,4-dimethoxyphenyl)-3-phthalimidopropionamide;

3-(3-ethoxy-4-methoxyphenyl)-N-hydroxy-3-(3-nitrophthalimido)propionamide;

N-hydroxy-3-(3,4-dimethoxyphenyl)-3-(1-oxoisoindolinyl) propionamide;

3-(3-ethoxy-4-methoxyphenyl)-N-hydroxy-3-(4-methylphthalimido)propionamide;

3-(3-cyclopentyloxy-4-methoxyphenyl)-N-hydroxy-3-phthalimidopropionamide;

3-(3-ethoxy-4-methoxyphenyl)-N-hydroxy-3-(1,3-dioxo-2,3-dihydro-1H-benzo[f]isoindol-2-yl)propionamide;

N-hydroxy-3-{3-(2-propoxy)-4-methoxyphenyl}-3-phthalimidopropionamide;

3-(3-ethoxy-4-methoxyphenyl)-3-(3,6-difluorophthalimido)-N-hydroxypropionamide;

3-(4-aminophthalimido)-3-(3-ethoxy-4-methoxyphenyl)-N-hydroxypropionamide;

3-(3-aminophthalimido)-3-(3-ethoxy-4-methoxyphenyl)-N-hydroxypropionamide;

3-(3-acetoamidophthalimido)-3-(3-ethoxy-4-methoxyphenyl)-N-hydroxypropionamide;

N-hydroxy-3-(3,4-dimethoxyphenyl)-3-(1-oxoisoindolinyl) propionamide;

3-(3-cyclopentyloxy-4-methoxyphenyl)-N-hydroxy-3-(1-oxoisoindolinyl) propionamide; or N-benzyloxy-3-(3-ethoxy-4-methoxyphenyl)-3-(3-nitrophthalimido)propionamide.

Other PDE4 modulators include the substituted phenethylsulfones substituted on the phenyl group with an oxoisoindine group. Examples of such compounds include, but are not limited to, those disclosed in U.S. Pat. No. 6,020,358, which is incorporated herein by reference, which include the following compounds of formula (X5):

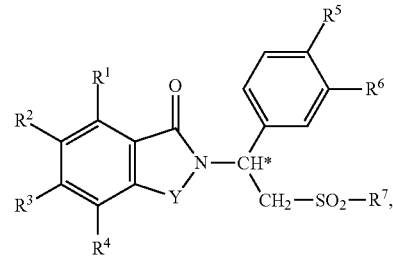

or a pharmaceutically acceptable salt, solvate, hydrate, clathrate, stereoisomer, or prodrug thereof, wherein compounds of formula (X5):

the carbon atom designated * constitutes a center of chirality;

Y is C=O, $CH_2$, $SO_2$, or $CH_2C$=O; each of $R^1$, $R^2$, $R^3$, and $R^4$, independently of the others, is hydrogen, halo, alkyl of 1 to 4 carbon atoms, alkoxy of 1 to 4 carbon atoms, nitro, cyano, hydroxy, or —$NR^8R^9$; or any two of $R^1$, $R^2$, $R^3$, and $R^4$ on adjacent carbon atoms, together with the depicted phenylene ring are naphthylidene;

each of $R^5$ and $R^6$, independently of the other, is hydrogen, alkyl of 1 to 4 carbon atoms, alkoxy of 1 to 4 carbon atoms, cyano, or cycloalkoxy of up to 18 carbon atoms;

$R^7$ is hydroxy, alkyl of 1 to 8 carbon atoms, phenyl, benzyl, or $NR^{8'}R^{9'}$;

each of $R^8$ and $R^9$ taken independently of the other is hydrogen, alkyl of 1 to 8 carbon atoms, phenyl, or benzyl; or one of $R^8$ and $R^9$ is hydrogen and the other is —$COR^{10}$ or —$SO_2R^{10}$; or $R^8$ and $R^9$ taken together are tetramethylene, pentamethylene, hexamethylene, or —CH$_2$CH$_2$X$^1$CH$_2$CH$_2$— in which X$^1$ is —O—, —S— or —NH—; and each of R$^{8'}$ and R$^{9'}$ taken independently of the other is hydrogen, alkyl of 1 to 8 carbon atoms, phenyl, or benzyl; or one of R$^{8'}$ and R$^{9'}$ is hydrogen and the other is —COR$^{10'}$ or —SO$_2$R$^{10'}$; or R$^{8'}$ and R$^{9'}$ taken together are tetramethylene, pentamethylene, hexamethylene, or —CH$_2$CH$_2$X$^2$CH$_2$CH$_2$— in which X$^2$ is —O—, —S—, or —NH—.

It will be appreciated that while for convenience the above compounds are identified as phenethylsulfones, compounds of formula (X5) include sulfonamides when R$^7$ is NR$^{8'}$R$^{9'}$.

In some embodiments, the compounds of formula (X5) are those in which Y is C=O or CH$_2$.

In other embodiments, the compounds of formula (X5) are those in which each of R$^1$, R$^2$, R$^3$, and R$^4$ independently of the others, is hydrogen, halo, methyl, ethyl, methoxy, ethoxy, nitro, cyano, hydroxy, or —NR$^8$R$^9$ in which each of R$^8$ and R$^9$ taken independently of the other is hydrogen or methyl or one of R$^8$ and R$^9$ is hydrogen and the other is —COCH$_3$.

In other embodiments, the compounds of formula (X5) are those in which one of R$^1$, R$^2$, R$^3$, and R$^4$ is —NH$_2$ and the remaining of R$^1$, R$^2$, R$^3$, and R$^4$ are hydrogen.

In other embodiments, the compounds of formula (X5) are those in which one of R$^1$, R$^2$, R$^3$, and R$^4$ is —NHCOCH$_3$ and the remaining of R$^1$, R$^2$, R$^3$, and R$^4$ are hydrogen.

In other embodiments, the compounds of formula (X5) are those in which one of R$^1$, R$^2$, R$^3$, and R$^4$ is —N(CH$_3$)$_2$ and the remaining of R$^1$, R$^2$, R$^3$, and R$^4$ are hydrogen.

In other embodiments, the compounds of formula (X5) are those in which one of R$^1$, R$^2$, R$^3$, and R$^4$ is methyl and the remaining of R$^1$, R$^2$, R$^3$, and R$^4$ are hydrogen.

In other embodiments, the compounds of formula (X5) are those in which one of R$^1$, R$^2$, R$^3$, and R$^4$ is fluoro and the remaining of R$^1$, R$^2$, R$^3$, and R$^4$ are hydrogen.

In other embodiments, the compounds of formula (X5) are those in which each of R$^5$ and R$^6$, independently of the other, is hydrogen, methyl, ethyl, propyl, methoxy, ethoxy, propoxy, cyclopentoxy, or cyclohexoxy.

In other embodiments, the compounds of formula (X5) are those in which R$^5$ is methoxy and R$^6$ is monocycloalkoxy, polycycloalkoxy, and benzocycloalkoxy.

In other embodiments, the compounds of formula (X5) are those in which R$^5$ is methoxy and R$^6$ is ethoxy.

In other embodiments, the compounds of formula (X5) are those in which R$^7$ is hydroxy, methyl, ethyl, phenyl, benzyl, or NR$^{8'}$R$^{9'}$ in which each of R$^{8'}$ and R$^{9'}$ taken independently of the other is hydrogen or methyl.

In other embodiments, the compounds of formula (X5) are those in which R$^7$ is methyl, ethyl, phenyl, benzyl or NR$^{8'}$ R$^{9'}$ in which each of R$^{8'}$ and R$^{9'}$ taken independently of the other is hydrogen or methyl.

In other embodiments, the compounds of formula (X5) are those in which R$^7$ is methyl.

In other embodiments, the compounds of formula (X5) are those in which R$^7$ is NR$^{8'}$ R$^{9'}$ in which each of R$^{8'}$ and R$^{9'}$ taken independently of the other is hydrogen or methyl.

Other PDE4 modulators include fluoroalkoxy-substituted 1,3-dihydro-isoindolyl compounds disclosed in U.S. Pat. No. 7,173,058, which is incorporated herein by reference. Representative compounds include those of formula (X6):

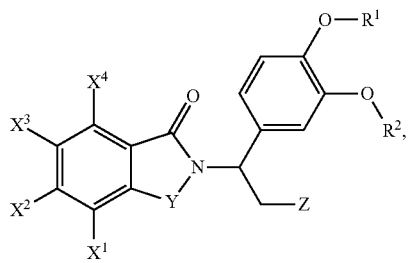

or a pharmaceutically acceptable salt, solvate, hydrate, clathrate, stereoisomer, or prodrug thereof, wherein compounds of formula (X6):

Y is —C(O)—, —CH$_2$, —CH$_2$C(O)—, —C(O)CH$_2$—, or SO$_2$;

Z is —H, —C(O)R$^3$, —(C$_{0-1}$-alkyl)-SO$_2$—(C$_{1-4}$-alkyl), —C$_{1-8}$-alkyl, —CH$_2$OH, CH$_2$(O)(C$_{1-8}$-alkyl) or —CN;

R$^1$ and R$^2$ are each independently —CHF$_2$, —C$_{1-8}$-alkyl, —C$_{3-18}$-cycloalkyl, or —(C$_{1-10}$-alkyl)(C$_{3-18}$-cycloalkyl), and at least one of R$_1$ and R$_2$ is CHF$_2$;

R$^3$ is —NR$^4$R$^5$, -alkyl, —OH, —O-alkyl, phenyl, benzyl, substituted phenyl, or substituted benzyl;

R$^4$ and R$^5$ are each independently —H, —C$_{1-8}$-alkyl, —OH, or —OC(O)R$^6$;

R$^6$ is —C$_{1-8}$-alkyl, -amino(C$_{1-8}$-alkyl), -phenyl, -benzyl, or -aryl;

X$^1$, X$^2$, X$^3$, and X$^4$ are each independently —H, -halogen, -nitro, —NH$_2$, —CF$_3$, —C$_{1-6}$-alkyl, —(C$_{0-4}$-alkyl)-(C$_{3-6}$-cycloalkyl), (C$_{0-4}$-alkyl)-NR$^7$R$^8$, (C$_{0-4}$-alkyl)-N(H)C(O)—(R$^8$), (C$_{0-4}$-alkyl)-N(H)C(O)N(R$^7$R$^8$), (C$_{0-4}$-alkyl)-N(H)C(O)O(R$^7$R$^8$), (C$_{0-4}$-alkyl)-OR$^8$, (C$_{0-4}$-alkyl)-imidazolyl, (C$_{0-4}$-alkyl)-pyrrolyl, (C$_{0-4}$-alkyl)-oxadiazolyl, or (C$_{0-4}$-alkyl)-triazolyl, or two of X$^1$, X$^2$, X$^3$, and X$^4$ may be joined together to form a cycloalkyl or heterocycloalkyl ring, (e.g., X$^1$ and X$^2$, X$^2$ and X$^3$, X$^3$ and X$^4$, X$^1$ and X$^3$, X$^2$ and X$^4$, or X$^1$ and X$^4$ may form a 3, 4, 5, 6, or 7 membered ring which may be aromatic, thereby forming a bicyclic system with the isoindolyl ring); and R$^7$ and R$^8$ are each independently H, C$_{1-9}$-alkyl, C$_{3-6}$-cycloalkyl, (C$_{1-6}$-alkyl)-(C$_{3-6}$-cycloalkyl), (C$_{1-6}$-alkyl)-N(R$^7$R$^8$), (C$_{1-6}$-alkyl)-OR$^8$, phenyl, benzyl, or aryl.

Other PDE4 modulators include the enantiomerically pure compounds disclosed in U.S. Pat. No. 6,962,940; international patent publication nos. WO 2003/080048 and WO 2003/080049; U.S. Pat. No. 7,312,241 to G. Muller et al.; and U.S. patent publication no. 2004/0167199A1, published Aug. 26, 2004, all of which are incorporated herein by reference. In certain embodiments, the compounds are an enantiomer of 2-[1-(3-ethoxy-4-methoxyphenyl)-2-methylsulfonylethyl]-4-acetylaminoisoindoline-1,3-dione and an enantiomer of 3-(3,4-dimethoxy-phenyl)-3-(1-oxo-1,3-dihydro-isoindol-2-yl)-propionamide.

In certain embodiments, the PDE4 modulators provided herein are 3-(3,4-dimethoxy-phenyl)-3-(1-oxo-1,3-dihydro-isoindol-2-yl)-propionamide and cyclopropanecarboxylic acid {2-[1-(3-ethoxy-4-methoxy-phenyl)-2-methanesulfonyl-ethyl]-3-oxo-2,3-dihydro-1H-isoindol-4-yl}-amide, which are available from Celgene Corp., Warren, N.J. 3-(3,4-Dimethoxy-phenyl)-3-(1-oxo-1,3-dihydro-isoindol-2-yl)-propionamide has the following chemical structure:

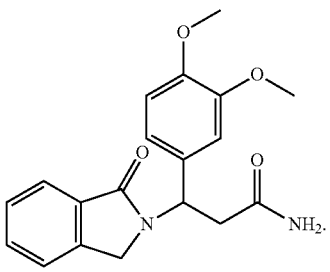 [SMILES: COc1ccc(C(CC(N)=O)N2Cc3ccccc3C2=O)cc1OC]

Other PDE4 modulators include, but are not limited to, the cycloalkyl amides and cycloalkyl nitriles of U.S. Pat. Nos. 5,728,844, 5,728,845, 5,968,945, 6,180,644 and 6,518,281, and WO 97/08143 and WO 97/23457, each of which is incorporated herein by reference. Representative compounds include those of formula (X7):

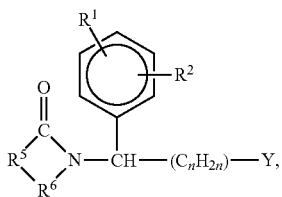

or a pharmaceutically acceptable salt, solvate, hydrate, clathrate, stereoisomer, or prodrug thereof, wherein compounds of formula (X7):

one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl, bicycloalkyl, or benzocycloalkyl of up to 18 carbon atoms;

X is a carbon-carbon bond, —CH$_2$—, or —O—;

$R^5$ is (i) o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, and lower alkoxy; (ii) a vicinally divalent residue of pyridine, pyrrolidine, imidazole, naphthalene, or thiophene, wherein the divalent bonds are on vicinal ring carbon atoms; (iii) a vicinally divalent cycloalkyl or cycloalkenyl of 4-10 carbon atoms, unsubstituted or substituted with 1 to 3 substituents each selected independently from the group consisting of nitro, cyano, halo, trifluoromethyl, carbo(lower)alkoxy, acetyl, carbamoyl, acetoxy, carboxy, hydroxy, amino, lower alkylamino, lower alkyl, lower alkoxy, or phenyl; (iv) vinylene di-substituted with lower alkyl; or (v) ethylene, unsubstituted or monosubstituted or disubstituted with lower alkyl;

$R^6$ is —CO—, —CH$_2$—, or —CH$_2$CO—;

Y is —COZ, —C≡N, —OR$^8$, lower alkyl, or aryl;

Z is —NH$_2$, —OH, —NHR, —R$^9$, or —OR$^9$ $R^8$ is hydrogen or lower alkyl;

$R^9$ is lower alkyl or benzyl; and n has a value of 0, 1, 2, or 3.

In one embodiment compounds of formula (X7), one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl of up to 10 carbon atoms, polycycloalkyl of up to 10 carbon atoms, or benzocyclic alkyl of up to 10 carbon atoms;

X is —CH$_2$— or —O—;

$R^5$ is (i) the vicinally divalent residue of pyridine, pyrrolidine, imidazole, naphthalene, or thiophene, wherein the two bonds of the divalent residue are on vicinal ring carbon atoms;

(ii) a vicinally divalent cycloalkyl of 4-10 carbon atoms, unsubstituted or substituted with 1 to 3 substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, and phenyl;

(iii) di-substituted vinylene, substituted with nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

(iv) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, and halo;

$R^6$ is —CO—, —CH$_2$—, or —CH$_2$CO—;

Y is —COX, —C≡N, —OR$^8$, alkyl of 1 to 5 carbon atoms, or aryl;

X is —NH$_2$, —OH, —NHR, —R$^9$, —OR$^9$, or alkyl of 1 to 5 carbon atoms;

$R^8$ is hydrogen or lower alkyl;

$R^9$ is alkyl or benzyl; and, n has a value of 0, 1, 2, or 3.

In another embodiment of the compounds of formula (X7), one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, HF$_2$CO, F$_3$CO, or $R^3$—X—;

$R^3$ is monocycloalkyl, bicycloalkyl, benzocyclo alkyl of up to 18 carbon atoms, tetrahydropyran, or tetrahydrofuran;

X is a carbon-carbon bond, —CH$_2$—, —O—, or —N=;

$R^5$ is (i) o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, and lower alkoxy; (ii) a vicinally divalent residue of pyridine, pyrrolidine, imidazole, naphthalene, or thiophene, wherein the divalent bonds are on vicinal ring carbon atoms; (iii) a vicinally divalent cycloalkyl or cycloalkenyl of 4-10 carbon atoms, unsubstituted or substituted with 1 or more substituents each selected independently from the group consisting of nitro, cyano, halo, trifluoromethyl, carbo(lower)alkoxy, acetyl, carbamoyl, acetoxy, carboxy, hydroxy, amino, lower alkylamino, lower alkyl, lower alkoxy, and phenyl; (iv) vinylene di-substituted with lower alkyl; or (v) ethylene, unsubstituted or monosubstituted or disubstituted with lower alkyl;

$R^6$ is —CO—, —CH$_2$—, or —CH$_2$CO—;

Y is —COX, —C≡N, —OR$^8$, alkyl of 1 to 5 carbon atoms, or aryl;

X is —NH$_2$, —OH, —NHR, —R$^9$, —OR$^9$, or alkyl of 1 to 5 carbon atoms;

$R^8$ is hydrogen or lower alkyl;

$R^9$ is alkyl or benzyl; and, n has a value of 0, 1, 2, or 3.

Other representative compounds include those of formula (X8):

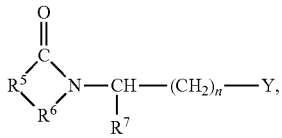

or a pharmaceutically acceptable salt, solvate, hydrate, clathrate, stereoisomer, or prodrug thereof, wherein compounds of formula (X8):

Y is —C≡N or $CO(CH_2)_mCH_3$;

m is 0, 1, 2, or 3;

$R^5$ is (i) o-phenylene, unsubstituted or substituted with 1 to 3 substituents each selected independently from nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, and halo; (ii) the divalent residue of pyridine, pyrrolidine, imidizole, naphthalene, or thiophene, wherein the divalent bonds are on vicinal ring carbon atoms; (iii) a divalent cycloalkyl of 4-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl and halo; (iv) di-substituted vinylene, substituted with nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or (v) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, and halo;

$R^6$ is —CO—, —$CH_2$—, —$CH_2CO$—, or —$SO_2$—;

$R^7$ is (i) straight or branched alkyl of 1 to 12 carbon atoms; (ii) cyclic or bicyclic alkyl of 1 to 12 carbon atoms; (iii) pyridyl; (iv) phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight, branched, cyclic, or bicyclic alkyl of 1 to 10 carbon atoms, straight, branched, cyclic, or bicyclic alkoxy of 1 to 10 carbon atoms, $CH_2R$ where R is a cyclic or bicyclic alkyl of 1 to 10 carbon atoms, and halo; (v) benzyl substituted with one to three substituents each selected independently from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 10 carbon atoms, and halo; (vi) naphthyl; or (vii) benzyloxy; and n has a value of 0, 1, 2, or 3.

In another embodiment, the PDE4 modulators include those of formula (X9):

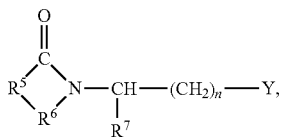

or a pharmaceutically acceptable salt, solvate, hydrate, clathrate, stereoisomer, or prodrug thereof, wherein compounds of formula (X9):

$R^5$ is (i) the divalent residue of pyridine, pyrrolidine, imidizole, naphthalene, or thiophene, wherein the divalent bonds are on vicinal ring carbon atoms; (ii) a divalent cycloalkyl of 4-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl and halo; (iii) di-substituted vinylene, substituted with nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or (iv) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

$R^6$ is —CO—, —$CH_2$—, —$CH_2CO$—, or —$SO_2$—;

$R^7$ is (i) cyclic or bicyclic alkyl of 4 to 12 carbon atoms; (ii) pyridyl; (iii) phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight, branched, cyclic, or bicyclic alkyl of 1 to 10 carbon atoms, straight, branched, cyclic, or bicyclic alkoxy of 1 to 10 carbon atoms, $CH_2R$ where R is a cyclic or bicyclic alkyl of 1 to 10 carbon atoms, or halo; (iv) benzyl substituted with one to three substituents each selected independently from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 10 carbon atoms, and halo; (v) naphthyl; or (vi) benzyloxy; and Y is COX, —C≡N, $OR^8$, alkyl of 1 to 5 carbon atoms, or aryl;

X is —$NH_2$, —OH, —NHR, —$R^9$, —$OR^9$, or alkyl of 1 to 5 carbon atoms;

$R^8$ is hydrogen or lower alkyl;

$R^9$ is alkyl or benzyl; and n has a value of 0, 1, 2, or 3.

Other PDE4 modulators include, but are not limited to, the aryl amides (for example, an embodiment being N-benzoyl-3-amino-3-(3',4'-dimethoxyphenyl)-propanamide) of U.S. Pat. Nos. 5,801,195, 5,736,570, 6,046,221 and 6,284,780, each of which is incorporated herein by reference. Representative compounds include those of formula (X10):

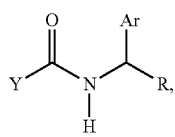

or a pharmaceutically acceptable salt, solvate, hydrate, clathrate, stereoisomer, or prodrug thereof, wherein compounds of formula (X10):

Ar is (i) straight, branched, or cyclic, unsubstituted alkyl of 1 to 12 carbon atoms; (ii) straight, branched, or cyclic, substituted alkyl of 1 to 12 carbon atoms; (iii) phenyl; (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, and halo; (v) heterocycle; or (vi) heterocycle substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

R is —H, alkyl of 1 to 10 carbon atoms, $CH_2OH$, $CH_2CH_2OH$, or $CH_2COZ$ where Z is alkoxy of 1 to 10 carbon atoms, benzyloxy, or $NHR^1$ where $R^1$ is H or alkyl of 1 to 10 carbon atoms; and Y is i) a phenyl or heterocyclic ring, unsubstituted or substituted one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo; or ii) naphthyl.

Other examples of the compounds include those of formula (X11):

or a pharmaceutically acceptable salt, solvate, hydrate, clathrate, stereoisomer, or prodrug thereof, wherein compounds of formula (X11):

Ar is 3,4-disubstituted phenyl where each substituent is selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

Z is alkoxy of 1 to 10 carbon atoms, benzyloxy, amino, or alkylamino of 1 to 10 carbon atoms; and Y is (i) a phenyl, unsubstituted or substituted with one or more substituents each selected, independently one from the other, from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, or (ii) naphthyl.

Other PDE4 modulators include, but are not limited to, the imide/amide ethers and alcohols (for example, 3-phthalimido-3-(3',4'-dimethoxyphenyl) propan-1-ol) disclosed in U.S. Pat. No. 5,703,098, which is incorporated herein by reference. Examples include compounds the formula (X12):

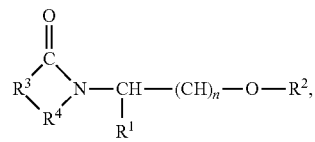

or a pharmaceutically acceptable salt, solvate, hydrate, clathrate, stereoisomer, or prodrug thereof, wherein compounds of formula (X12):

$R^1$ is (i) straight, branched, or cyclic, unsubstituted alkyl of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, acylamino, alkylamino, di(alkyl) amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, and halo;

$R^2$ is hydrogen, alkyl of 1 to 8 carbon atoms, benzyl, pyridylmethyl, or alkoxymethyl;

$R^3$ is (i) ethylene, (ii) vinylene, (iii) a branched alkylene of 3 to 10 carbon atoms, (iv) a branched alkenylene of 3 to 10 carbon atoms, (v) cycloalkylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vi) cycloalkenylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vii) o-phenylene unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (viii) naphthyl, or (ix) pyridyl;

$R^4$ is —CX—, —$CH_2$— or —$CH_2CX$—;

X is O or S; and n is 0, 1, 2, or 3.

Other PDE4 modulators include, but are not limited to, the succinimides and maleimides (for example methyl 3-(3',4',5'6'-petrahydrophthalimdo)-3-(3",4"-dimethoxyphenyl) propionate) disclosed in U.S. Pat. No. 5,658,940, which is incorporated herein by reference. Examples include compounds of formula (X13):

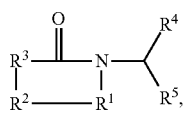

or a pharmaceutically acceptable salt, solvate, hydrate, clathrate, stereoisomer, or prodrug thereof, wherein compounds of formula (X13):

$R^1$ is —CH$_2$—, —CH$_2$CO—, or —CO—;

$R^2$ and $R^3$ taken together are (i) ethylene unsubstituted or substituted with alkyl of 1-10 carbon atoms or phenyl, (ii) vinylene substituted with two substituents each selected, independently of the other, from the group consisting of alkyl of 1-10 carbon atoms and phenyl, or (iii) a divalent cycloalkyl of 5-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl unsubstituted or substituted with alkyl of 1-3 carbon atoms, acetoxy, carboxy, hydroxy, amino, substituted amino, alkyl of 1 to 10 carbon atoms, alkoxy of 1 to 10 carbon atoms, norbornyl, phenyl and halo;

$R^4$ is (i) straight or branched unsubstituted alkyl of 4 to 8 carbon atoms; (ii) cycloalkyl or bicycloalkyl of 5-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, branched, straight or cyclic alkyl of 1 to 10 carbon atoms, alkoxy of 1 to 10 carbon atoms, phenyl and halo; (iii) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, cycloalkyl or bicycloalkyl of 3 to 10 carbon atoms, cycloalkoxy or bicycloalkoxy of 3 to 10 carbon atoms, phenyl and halo; (iv) pyridine or pyrrolidine, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl and halo;

$R^5$ is —COX, —CN, —CH$_2$COX, alkyl of 1 to 5 carbon atoms, aryl, —CH$_2$OR, —CH$_2$ aryl, or —CH$_2$OH, X is NH$_2$, OH, NHR, or OR$^6$, R is lower alkyl; and $R^6$ is alkyl or benzyl.

Other PDE4 modulators include, but are not limited to, substituted imides (for example, 2-phthalimido-3-(3',4'-dimethoxyphenyl) propane) disclosed in U.S. Pat. No. 6,429,221, which is incorporated herein by reference. Examples include compounds of the formula (X14):

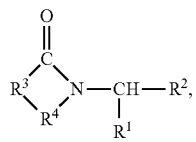

or a pharmaceutically acceptable salt, solvate, hydrate, clathrate, stereoisomer, or prodrug thereof, wherein compounds of formula (X14):

$R^1$ is (i) straight, branched, or cyclic alkyl of 1 to 12 carbon atoms; (ii) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight or branched alkyl of 1 to 10 carbon atoms, alkoxy of 1 to 10 carbon atoms, and halo; (iii) benzyl or benzyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, or (iv) —Y-Ph where Y is a straight, branched, or cyclic alkyl of 1 to 12 carbon atoms and Ph is phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

$R^2$ is —H, a branched or unbranched alkyl of 1 to 10 carbon atoms, phenyl, pyridyl, heterocycle, —CH$_2$-aryl, or —CH$_2$-heterocycle;

$R^3$ is i) ethylene; ii) vinylene; iii) a branched alkylene of 3 to 10 carbon atoms; iv) a branched alkenylene of 3 to 10 carbon atoms; v) cycloalkylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, and halo; vi) cycloalkenylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo; or vii) o-phenylene unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy 1 to 4 carbon atoms, and halo;

$R^4$ is —CX, or —CH$_2$—; and

X is O or S.

Other PDE4 modulators include, but are not limited to, substituted 1,3,4-oxadiazoles (for example, 2-[1-(3-cyclopentyloxy-4-methoxyphenyl)-2-(1,3,4-oxadiazole-2-yl) ethyl]-5-methylisoindoline-1,3-dione) disclosed in U.S. Pat. No. 6,326,388, which is incorporated herein by reference. Examples include compounds of formula (X15):

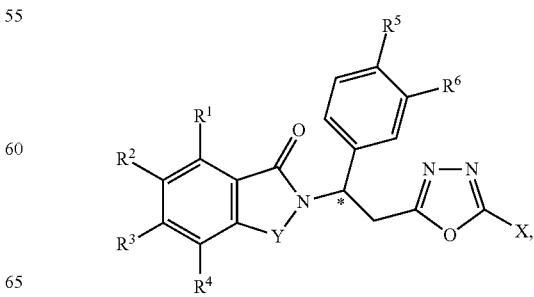

or a pharmaceutically acceptable salt, solvate, hydrate, clathrate, stereoisomer, or prodrug thereof, wherein compounds of formula (X15):

the carbon atom designated* constitutes a center of chirality;

Y is C=O, CH$_2$, SO$_2$ or CH$_2$C=O;

X is hydrogen, or alkyl of 1 to 4 carbon atoms;

each of R$^1$, R$^2$, R$^3$, and R$^4$, independently of the others, is hydrogen, halo, trifluoromethyl, acetyl, alkyl of 1 to 8 carbon atoms, alkoxy of 1 to 4 carbon atoms, nitro, cyano, hydroxy, —CH$_2$NR$^8$R$^9$, —(CH$_2$)$_2$NR$^8$R$^9$, or —NR$^8$R$^9$ or any two of R$^1$, R$^2$, R$^3$, and R$^4$ on adjacent carbon atoms, together with the depicted benzene ring are naphthylidene, quinoline, quinoxaline, benzimidazole, benzodioxole or 2-hydroxybenzimidazole;

each of R$^5$ and R$^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicycloalkoxy of up to 18 carbon atoms, tricycloalkoxy of up to 18 carbon atoms, or cycloalkylalkoxy of up to 18 carbon atoms;

each of R$^8$ and R$^9$, taken independently of the other is hydrogen, straight or branched alkyl of 1 to 8 carbon atoms, phenyl, benzyl, pyridyl, or pyridylmethyl; or one of R$^8$ and R$^9$ is hydrogen and the other is —COR$^{10}$, or —SO$_2$R$^{10}$; or R$^8$ and R$^9$ taken together are tetramethylene, pentamethylene, hexamethylene, —CH=NCH=CH—, or —CH$_2$CH$_2$X$^1$CH$_2$CH$_2$— in which X$^1$ is —O—, —S—, or —NH—;

R$^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, NR$^{11}$R$^{12}$, CH$_2$NR$^{14}$R$^{15}$, or NR$^{11}$R$^{12}$;

R$^{14}$ and R$^{15}$, independently of each other, are hydrogen, methyl, ethyl, or propyl; and R$^{11}$ and R$^{12}$, independently of each other, are hydrogen, alkyl of 1 to 8 carbon atoms, phenyl, or benzyl.

In certain embodiments, the compounds include those of formula (X16):

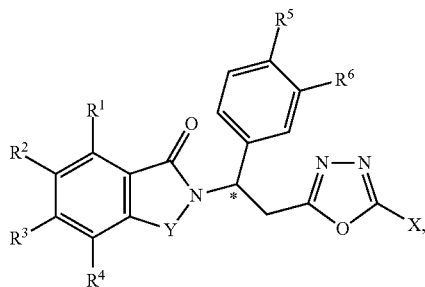

or a pharmaceutically acceptable salt, solvate, hydrate, clathrate, stereoisomer, or prodrug thereof, wherein compounds of formula (X16):

the carbon atom designated* constitutes a center of chirality;

Y is C=O, CH$_2$, SO$_2$ or CH$_2$C=O;

X is hydrogen, or alkyl of 1 to 4 carbon atoms;

(i) each of R$^1$, R$^2$, R$^3$, and R$^4$, independently of the others, is hydrogen, halo, trifluoromethyl, acetyl, alkyl of 1 to 8 carbon atoms, alkoxy of 1 to 4 carbon atoms, nitro, cyano, hydroxy, —CH$_2$NR$^8$R$^9$, —(CH$_2$)$_2$NR$^8$R$^9$, or —NR$^8$R$^9$; or (ii) any two of R$^1$, R$^2$, R$^3$, and R$^4$ on adjacent carbon atoms, together with the depicted benzene ring to which they are bound are naphthylidene, quinoline, quinoxaline, benzimidazole, benzodioxole or 2-hydroxybenzimidazole;

each of R$^5$ and R$^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicycloalkoxy of up to 18 carbon atoms, tricycloalkoxy of up to 18 carbon atoms, or cycloalkylalkoxy of up to 18 carbon atoms;

(i) each of R$^8$ and R$^9$, independently of the other, is hydrogen, alkyl of 1 to 8 carbon atoms, phenyl, benzyl, pyridyl, or pyridylmethyl; or (ii) one of R$^8$ and R$^9$ is hydrogen and the other is —COR$^{10}$ or —SO$_2$R$^{10}$, in which R$^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, or NR$^{11}$R$^{12}$, or CH$_2$NR$^{14}$R$^{15}$, wherein R$^{11}$ and R$^{12}$, independently of each other, are hydrogen, alkyl of 1 to 8 carbon atoms, phenyl, or benzyl and R$^{14}$ and R$^{15}$, independently of each other, are hydrogen, methyl, ethyl, or propyl; or (iii) R$^8$ and R$^9$ taken together are tetramethylene, pentamethylene, hexamethylene, —CH=NCH=CH—, or —CH$_2$CH$_2$X$^1$CH$_2$CH$_2$,- in which X$^1$ is —O—, —S—, or —NH—.

Other PDE4 modulators include, but are not limited to, cyano and carboxy derivatives of substituted styrenes (for example, 3,3-bis-(3,4-dimethoxyphenyl) acrylonitrile) disclosed in U.S. Pat. Nos. 5,929,117, 6,130,226, 6,262,101 and 6,479,554, each of which is incorporated herein by reference. Examples include compounds of formula (X17):

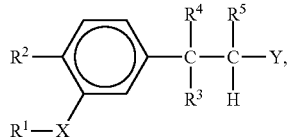

or a pharmaceutically acceptable salt, solvate, hydrate, clathrate, stereoisomer, or prodrug thereof, wherein compounds of formula (X17):

(a) X is —O— or —(C$_n$H$_{2n}$)— in which n has a value of 0, 1, 2, or 3, and R$^1$ is alkyl of one to 10 carbon atoms, monocycloalkyl of up to 10 carbon atoms, polycycloalkyl of up to 10 carbon atoms, or benzocyclic alkyl of up to 10 carbon atoms; or (b) X is —CH= and R$^1$ is alkylidene of up to 10 carbon atoms, monocycloalkylidene of up to 10 carbon atoms, or bicycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

R$^3$ is (i) phenyl, unsubstituted or substituted with 1 or more substituents each selected independently from nitro, cyano, halo, trifluoromethyl, carbethoxy, carbomethoxy, carbopropoxy, acetyl, carbamoyl, carbamoyl substituted with alkyl of 1 to 3 carbon atoms, acetoxy, carboxy, hydroxy, amino, amino substituted with an alkyl of 1 to 5 carbon atoms, alkyl of up to 10 carbon atoms, cycloalkyl of up to 10 carbon atoms, alkoxy of up to 10 carbon atoms, cycloalkoxy of up to 10 carbon atoms, alkylidenemethyl of up to 10 carbon atoms, cycloalkylidenemethyl of up to 10 carbon atoms, phenyl, and methylenedioxy; (ii) pyridine, substituted pyridine, pyrrolidine, imidizole, naphthalene, or thiophene; (iii) cycloalkyl of 4-10 carbon atoms, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, and alkoxy of 1 to 10 carbon atoms, phenyl;

each of $R^4$ and $R^5$ taken individually is hydrogen; or $R^4$ and $R^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$; R$^6$ is hydrogen or lower alkyl; and R$^7$ is alkyl or benzyl.

In some embodiments, PDE4 modulators include compounds of formula (X18):

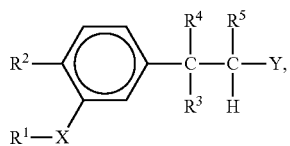

or a pharmaceutically acceptable salt, solvate, hydrate, clathrate, stereoisomer, or prodrug thereof, wherein compounds of formula (X18):

(a) X is —O— or —(C$_n$H$_{2n}$)— in which n has a value of 0, 1, 2, or 3, and $R^1$ is alkyl of one to 10 carbon atoms, monocycloalkyl of up to 10 carbon atoms, polycycloalkyl of up to 10 carbon atoms, or benzocyclic alkyl of up to 10 carbon atoms; or (b) X is —CH= and $R^1$ is alkylidene of up to 10 carbon atoms, monocycloalkylidene of up to 10 carbon atoms, or bicycloalkylidene of up to 10 carbon atoms;

$R^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

$R^3$ is pyrrolidine, imidazole or thiophene unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, and phenyl;

each of $R^4$ and $R^5$ taken individually is hydrogen; or $R^4$ and $R^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$; R$^6$ is hydrogen or lower alkyl; and R$^7$ is alkyl or benzyl.

In some embodiments, provided herein are compounds of the formula (X19):

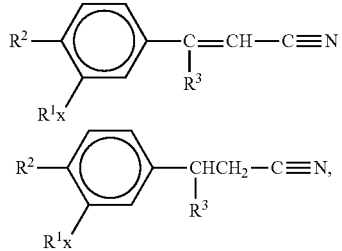

or a pharmaceutically acceptable salt, solvate, hydrate, clathrate, stereoisomer, or prodrug thereof, wherein compounds of formula (X19):

(a) X is —O— or —(C$_n$H$_{2n}$)— in which n has a value of 0, 1, 2, or 3, and $R^1$ is alkyl of up to 10 carbon atoms, monocycloalkyl of up to 10 carbon atoms, polycycloalkyl of up to 10 carbon atoms, or benzocyclic alkyl of up to 10 carbon atoms, or (b) X is —CH=, and $R^1$ is alkylidene of up to 10 carbon atoms or monocycloalkylidene of up to 10 carbon atoms;

$R^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, or halo; and $R^3$ is (i) phenyl or naphthyl, unsubstituted or substituted with 1 or more substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 5 carbon atoms, alkoxy and cycloalkoxy of 1 to 10 carbon atoms; or (ii) cycloalkyl of 4 to 10 carbon atoms, unsubstituted or substituted with one or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, and phenyl.

In one embodiment, the compound is of formula:

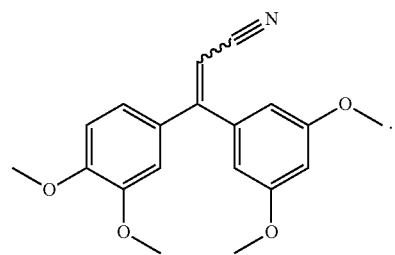

Other PDE4 modulators include, but are not limited to, isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606 and U.S. Pat. No. 6,667,316, which are incorporated herein by reference. Examples include compounds of formula (X20):

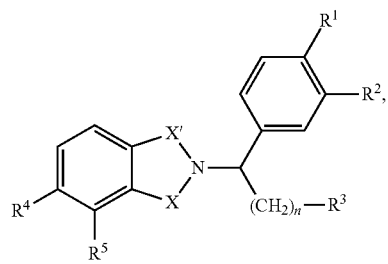

or a pharmaceutically acceptable salt, solvate, hydrate, clathrate, stereoisomer, or prodrug thereof, wherein compounds of formula (X20):

one of X and X' is =C=O or =SO$_2$, and the other of X and X' is =C=O, =CH$_2$, =SO$_2$ or =CH$_2$C=O;

n is 1, 2 or 3;

R$^1$ and R$^2$ are each independently (C$_1$-C$_4$)alkyl, (C$_1$-C$_4$) alkoxy, cyano, (C$_3$-C$_{18}$)cycloalkyl, (C$_3$-C$_{18}$)cycloalkoxy, or (C$_3$-C$_{18}$)cycloalkyl-methoxy;

R$^3$ is SO$_2$—Y, COZ, CN or (C$_1$-C$_6$)hydroxyalkyl, wherein:

Y is (C$_1$-C$_6$)alkyl, benzyl or phenyl;

Z is —NR$^6$R$^7$, (C$_1$-C$_6$)alkyl, benzyl or phenyl;

R$^6$ is H, (C$_1$-C$_4$)alkyl, (C$_3$-C$_{18}$)cycloalkyl, (C$_2$-C$_5$)alkanoyl, benzyl or phenyl, each of which may be optionally substituted with halo, amino or (C$_1$-C$_4$)alkyl-amino;

R$^7$ is H or (C$_1$-C$_4$)alkyl;

R$^4$ and R$^5$ are taken together to provide —NH—CH$_2$—R$^8$—, NH—CO—R$^8$—, or —N=CH—R$^8$—, wherein:

R$^8$ is CH$_2$, O, NH, CH=CH, CH=N, or N=CH; or one of R$^4$ and R$^5$ is H, and the other of R$_4$ and R$_5$ is imidazoyl, pyrrolyl, oxadiazolyl, triazolyl, or a structure of formula (A),

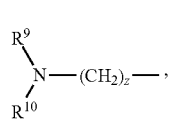

(A)

wherein:

z is 0 or 1;

R$^9$ is: H; (C$_1$-C$_4$)alkyl, (C$_3$-C$_{18}$)cycloalkyl, (C$_2$-C$_5$)alkanoyl, or (C$_4$-C$_6$)cycloalkanoyl, optionally substituted with halo, amino, (C$_1$-C$_4$)alkyl-amino, or (C$_1$-C$_4$)dialkylamino; phenyl; benzyl; benzoyl; (C$_2$-C$_5$)alkoxycarbonyl; (C$_3$-C$_5$) alkoxyalkylcarbonyl; N-morpholinocarbonyl; carbamoyl; N-substituted carbamoyl substituted with (C$_1$-C$_4$)alkyl; or methylsulfonyl; and R$^{10}$ is H, (C$_1$-C$_4$)alkyl, methylsulfonyl, or (C$_3$-C$_5$)alkoxyalkylcarbonyl; or R$^9$ and R$^{10}$ are taken together to provide —CH=CH—CH=CH—, —CH=CH—N=CH—, or (C$_1$-C$_2$)alkylidene, optionally substituted with amino, (C$_1$-C$_4$)alkyl-amino, or (C$_1$-C$_4$)dialkylamino; or R$^4$ and R$^5$ are both structures of formula (A).

In one embodiment of the compounds of formula (X20), z is not 0 when (i) R$^3$ is —SO$_2$—Y, —COZ, or —CN and (ii) one of R$^4$ or R$^5$ is hydrogen. In another embodiment of the compounds of formula (X20), R$^9$ and R$^{10}$, taken together, are —CH=CH—CH=CH—, —CH=CH—N=CH—, or (C$_1$-C$_2$)alkylidene substituted by amino, (C$_1$-C$_4$)alkyl-amino, or (C$_1$-C$_4$)dialkylamino. In another embodiment, R$^4$ and R$^5$ are both structures of formula (A).

In some embodiments, compounds useful in the inventions described herein include those of formula:

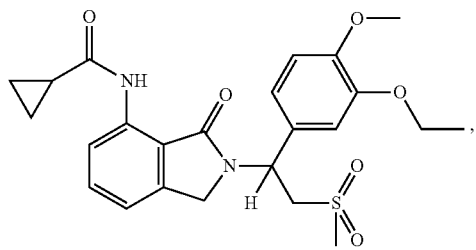

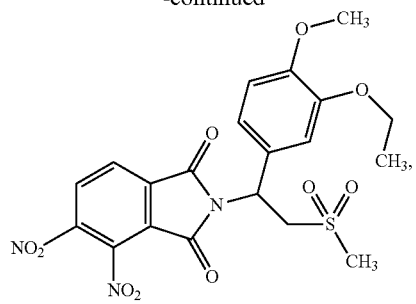

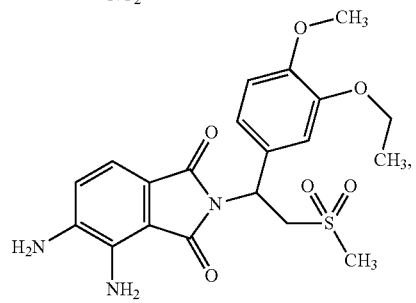

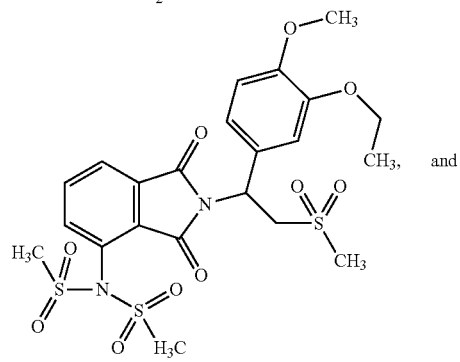

and

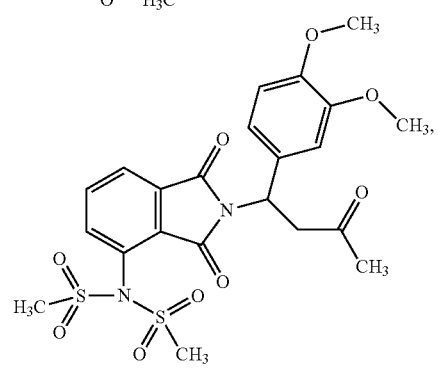

or a pharmaceutically acceptable salt, solvate, hydrate, clathrate, stereoisomer, or prodrug thereof.

Further examples include, but are not limited to: 2-[1-(3-Ethoxy-4-methoxyphenyl)-2-methylsulfonylethyl]-4,5-dinitroisoindoline-1,3-dione; 2-[1-(3-Ethoxy-4-methoxyphenyl)-2-methylsulfonylethyl]-4,5-diaminoisoindoline-1,3-dione; 7-[l-(3-Ethoxy-4-methoxyphenyl)-2-methylsulfonylethyl]-3-pyrrolino[3,4-e]benzimidazole-6,8-dione; 7-[1-(3-Ethoxy-4-methoxyphenyl)-2-methylsulfonylethyl]hydro-3-pyrrolino[3,4-e] benzimidazole-2,6,8-trione; 2-[1-(3-Ethoxy-4-methoxyphenyl)-2-methylsulfonylethyl]-3-pyrrolino[3,4-f] quinoxaline-1,3-dione; cyclopropyl-N-{2-[1-(3-ethoxy-4-methoxyphenyl)-2-methylsulfonylethyl]-1,3-dioxoisoindolin-4-yl}carboxamide; 2-Chloro-N-{2-[1-(3- ethoxy-4-methoxyphenyl)-2-methylsulfonylethyl]-1,3-dioxoisoindolin-4-yl}acetamide; 2-Amino-N-{2-[1-(3-ethoxy-4-methoxyphenyl)-2-methyl sulfonylethyl]-1,3-dioxoisoindolin-4-yl}acetamide; 2-N,N-Dimethylamino-N-{2-[-(3-ethoxy-4-methoxyphenyl)-2-methylsulfonylethyl]-1,3-dioxoisoindolin-4-yl}acetamide; N-{2-[1-(3-ethoxy-4-methoxyphenyl)-2-methylsulfonylethyl]-1,3-dioxoisoindolin-4-yl}-2,2,2-trifluoroacetamide; N-{2-[-(3-Ethoxy-4-methoxyphenyl)-2-methyl sulfonylethyl]-1,3-dioxoisoindinolin-4-yl}methoxycarboxamide; 4-[1-Aza-2-(dimethylamino)vinyl]-2-[1-(3-ethoxy-4-methoxyphenyl)-2-methylsulfonylethyl]isoindoline-1,3-dione; 4-[1-Aza-2-(dimethylamino)prop-1-enyl]-2-[1-(3-ethoxy-4-methoxyphenyl)-2-methylsulfonylethyl]isoindoline-1,3-dione; 2-[1-(3-Ethoxy-4-methoxyphenyl)-2-methylsulfonylethyl]-4-(5-methyl-1,3,4-oxadiazol-2-yl)isoindoline-1,3-dione; 2-[1-(3-Ethoxy-4-methoxyphenyl)-2-methylsulfonylethyl]-4-pyrrolylisoindoline-1,3-dione; 4-(Aminomethyl)-2-[1-(3-ethoxy-4-methoxyphenyl)-2-methylsulfonylethyl]-isoindoline-1,3-dione; 2-[1-(3-Ethoxy-4-methoxyphenyl)-2-methylsulfonylethyl]-4-(pyrrolylmethyl)isoindoline-1,3-dione; N-{2-[1-(3-ethoxy-4-methoxyphenyl)-3-hydroxybutyl]-1,3-dioxoisoindolin-4-yl}acetamide; N-{2-[1-(3-Ethoxy-4-methoxyphenyl)-3-oxobutyl]-1,3-dioxoisoindolin-4-yl}acetamide; N-{2-[1R-(3-ethoxy-4-methoxyphenyl)-3-hydroxybutyl]-1,3-dioxoisoindolin-4-yl}acetamide; N-{2-[1R-(3-ethoxy-4-methoxyphenyl)-3-oxobutyl]-1,3-dioxoisoindolin-4-yl}acetamide; N-{2-[1S-(3-Ethoxy-4-methoxyphenyl)-3-hydroxybutyl]-1,3-dioxoisoindolin-4-yl}acetamide; N-{2-[1 S-(3-ethoxy-4-methoxyphenyl)-3-oxobutyl]-1,3-dioxoisoindolin-4-yl}acetamide; 4-Amino-2-[1-(3-ethoxy-4-methoxyphenyl)-3-hydroxybutylisoindoline-1,3-dione; 4-Amino-2-[1-(3-ethoxy-4-methoxyphenyl)-3-oxobutyl]isoindoline-1,3-dione; 2-[1-(3-Ethoxy-4-methoxyphenyl)-3-oxobutyl]-4-pyrrolylisoindoline-1,3-dione; 2-Chloro-N-{2-[1-(3-ethoxy-4-methoxyphenyl)-3-oxobutyl]-1,3-dioxoisoindol-4-yl}acetamide; 2-(Dimethylamino)-N-{2-[1-(3-ethoxy-4-methoxyphenyl)-3-oxobutyl]-1,3-dioxoisoindolin-4-yl}acetamide; 4-Amino-2-[1R-(3-ethoxy-4-methoxyphenyl)-3-hydroxybutyl]isoindoline-1,3-dione; 4-Amino-2-[1R-(3-ethoxy-4-methoxyphenyl)-3-oxobutyl]isoindoline-1,3-dione; 2-[1R-(3-ethoxy-4-methoxyphenyl)-3-oxobutyl]-4-pyrrolylisoindoline-1,3-dione; 2-(Dimethylamino)-N-{2-[1R-(3-ethoxy-4-methoxyphenyl)-3-oxobutyl]-1,3-dioxoisoindolin-4-yl}acetamide; Cyclopentyl-N-{2-[1-(3-ethoxy-4-methoxyphenyl)-2-(methyl sulfonyl)ethyl]-1,3-dioxoisoindolin-4-yl}carboxamide; 3-(Dimethylamino)-N-{2-[1-(3-ethoxy-4-methoxyphenyl)-2-(methyl sulfonyl)ethyl]-1,3-dioxoisoindolin-4-yl}propanamide; 2-(Dimethylamino)-N-{2-[1-(3-ethoxy-4-methoxyphenyl)-2-(methylsulfonyl)ethyl]-1,3-dioxoisoindolin-4-yl}propanamide; N-{2-[(1R)-1-(3-ethoxy-4-methoxyphenyl)-2-(methylsulfonyl)ethyl]-1,3-dioxoisoindolin-4-yl}-2-(dimethylamino)acetamide; N-{2-[(1S)-1-(3-ethoxy-4-methoxyphenyl)-2-(methylsulfonyl)ethyl]-1,3-dioxoisoindolin-4-yl}-2-(dimethylamino)acetamide; 4-{3-[(Dimethylamino)methyl]pyrrolyl}-2-[1-(3-ethoxy-4-methoxyphenyl)-2-(methylsulfonyl)ethyl]isoindoline-1,3-dione; Cyclopropyl-N-{2-[(1S)-1-(3-ethoxy-4-methoxyphenyl)-2-(methylsulfonyl)ethyl]-1,3-dioxoisoindolin-4-yl}carboxamide; 2-[1-(3,4-dimethoxyphenyl)-2-(methylsulfonyl)ethyl]-4-pyrrolylisoindoline-1,3-dione; N-{2-[1-(3,4-dimethoxyphenyl)-2-(methylsulfonyl)ethyl]-1,3-dioxoisoindolin-4-yl}-2-(dimethylamino)acetamide; Cyclopropyl-N-{2-[1-(3,4-dimethoxyphenyl)-2-(methylsulfonyl)ethyl]-1,3-dioxoisoindolin-4-yl}carboxamide; Cyclopropyl-N-{2-[1-(3-ethoxy-4-methoxyphenyl)-2-(methylsulfonyl)ethyl]-3-oxoisoindolin-4-yl}carboxamide; 2-(Dimethylamino)-N-{2-[1-(3-ethoxy-4-methoxyphenyl)-2-(methylsulfonyl)ethyl]-3-oxoisoindolin-4-yl}acetamide; Cyclopropyl-N-{2-[(1S)-1-(3-ethoxy-4-methoxyphenyl)-2-(methylsulfonyl)ethyl]-3-oxoisoindolin-4-yl}carboxamide; Cyclopropyl-N-{2-[(1R)-1-(3-ethoxy-4-methoxyphenyl)-2-(methylsulfonyl)ethyl]-3-oxoisoindolin-4-yl}carboxamide; (3R)-3-[7-(Acetylamino)-1-oxoisoindolin-2-yl]-3-(3-ethoxy-4-methoxyphenyl)-N,N-dimethylpropanamide; (3R)-3-[7-(Cyclopropylcarbonylamino)-1-oxoisoindolin-2-yl]-3-(3-ethoxy-4-methoxyphenyl)-N,N-dimethylpropanamide; 3-{4-[2-(Dimethylamino)acetylamino]-1,3-dioxoisoindolin-2-yl}-3-(3-ethoxy-4-methoxyphenyl)-N,N-dimethylpropanamide; (3R)-3-[7-(2-Chloroacetylamino)-1-oxoisoindolin-2-yl]-3-(3-ethoxy-4-methoxy-phenyl)-N,N-dimethylpropanamide; (3R)-3-{4-[2-(dimethylamino)acetylamino]-1,3-dioxoisoindolin-2-yl}-3-(3-ethoxy-4-methoxyphenyl)-N,N-dimethylpropanamide; 3-(1,3-Dioxo-4-pyrrolylisoindolin-2-yl)-3-(3-ethoxy-4-methoxyphenyl)-N,N-dimethylpropanamide; 2-[1-(3-Ethoxy-4-methoxyphenyl)-2-(methyl sulfonyl)ethyl]-4-(imidazolylmethyl)isoindoline-1,3-dione; N-({2-[1-(3-Ethoxy-4-methoxyphenyl)-2-(methylsulfonyl)ethyl]-1,3-dioxoisoindolin-4-yl}methyl)acetamide; 2-Chloro-N-({2-[1-(3-ethoxy-4-methoxyphenyl)-2-(methylsulfonyl)ethyl]-1,3-dioxoisoindolin-4-yl}methyl)acetamide; 2-(Dimethylamino)-N-({2-[1-(3-ethoxy-4-methoxyphenyl)-2-(methylsulfonyl)ethyl]-1,3-dioxoisoindolin-4-yl}methyl)acetamide; 4-[Bis(methylsulfonyl)amino]-2-[1-(3-ethoxy-4-methoxyphenyl)-2-(methylsulfonyl)ethyl]isoindoline-1,3-dione; 2-[1-(3-Ethoxy-4-methoxyphenyl)-2-(methylsulfonyl)ethyl]-4-[(methylsulfonyl)amino]isoindoline-1,3-dione; N-{2-[1-(3-Ethoxy-4-methoxyphenyl)-3-hydroxypentyl]-1,3-dioxoisoindolin-4-yl}acetamide; N-{2-[1-(3-Ethoxy-4-methoxyphenyl)-3-oxopentyl]1,3-dioxoisoindolin-4-yl}acetamide; 2-[(1R)-1-(3-Ethoxy-4-methoxyphenyl)-3-hydroxybutyl]-4-(pyrrolylmethyl)isoindoline-1,3-dione; 2-[(1R)-1-(3-Ethoxy-4-methoxyphenyl)-3-oxobutyl]-4-(pyrrolylmethyl)isoindoline-1,3-dione; N-{2-[1-(3-Cyclopentyloxy-4-methoxyphenyl)-3-hydroxybutyl]-1,3-dioxoisoindolin-4-yl}acetamide; N-{2-[1-(3-Cyclopentyloxy-4-methoxyphenyl)-3-oxobutyl]-1,3-dioxoisoindolin-4-yl}acetamide; 2-[1-(3-Cyclopentyloxy-4-methoxyphenyl)-3-oxobutyl]-4-pyrrolylisoindoline-1,3-dione; 2-[1-(3,4-Dimethoxyphenyl)-3-oxobutyl]-4-[bis(methylsulfonyl)amino]isoindoline-1,3-dione; or a pharmaceutically acceptable salt, solvate, hydrate, clathrate, stereoisomer, or prodrug thereof.

Still other PDE4 modulators include, but are not limited to, imido and amido substituted acylhydroxamic acids (for example, (3-(1,3-dioxoisoindoline-2-yl)-3-(3-ethoxy-4-methoxyphenyl) propanoylamino) propanoate disclosed in WO 01/45702 and U.S. Pat. No. 6,699,899, which are incorporated herein by reference. Examples include compounds of formula (X21):

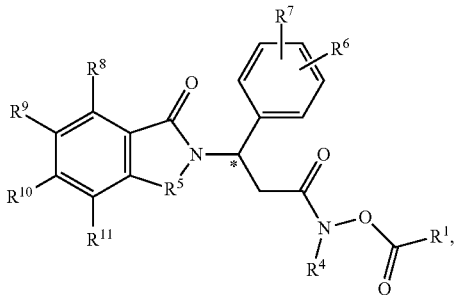

or a pharmaceutically acceptable salt, solvate, hydrate, clathrate, stereoisomer, or prodrug thereof, wherein compounds of formula (X21):

the carbon atom designated * constitutes a center of chirality, $R^4$ is hydrogen or —(C=O)—$R^{12}$, each of $R^1$ and $R^{12}$, independently of each other, is alkyl of 1 to 6 carbon atoms, phenyl, benzyl, pyridyl methyl, pyridyl, imidazoyl, imidazolyl methyl, or CHR*(CH$_2$)$_n$NR*R$^0$, wherein R* and $R^0$, independently of the other, are hydrogen, alkyl of 1 to 6 carbon atoms, phenyl, benzyl, pyridyl methyl, pyridyl, imidazoyl or imidazolylmethyl, and n=0, 1, or 2;

$R^5$ is C=O, CH$_2$, CH$_2$—CO—, or SO$_2$;

each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 6 carbon atoms, alkoxy of 1 to 6 carbon atoms, cycloalkoxy of 3 to 8 carbon atoms, halo, bicycloalkyl of up to 18 carbon atoms, tricycloalkoxy of up to 18 carbon atoms, 1-indanyloxy, 2-indanyloxy, $C_4$-$C_8$-cycloalkylidenemethyl, or $C_3$-$C_{10}$-alkylidenemethyl;

each of $R^8$, $R^9$, $R^{10}$, and $R^{11}$, independently of the others, is (i) hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, or alkoxy of 1 to 10 carbon atoms, halo; or (ii) one of $R^8$, $R^9$, $R^{10}$, and $R^{11}$ is acylamino comprising a lower alkyl, and the remaining of $R^8$, $R^9$, $R^{10}$, and $R^{11}$ are hydrogen; or (iii) hydrogen if $R^8$ and $R^9$ taken together are benzo, quinoline, quinoxaline, benzimidazole, benzodioxole, 2-hydroxybenzimidazole, methylenedioxy, dialkoxy, or dialkyl; or (iv) hydrogen if $R^{10}$ and $R^{11}$, taken together are benzo, quinoline, quinoxaline, benzimidazole, benzodioxole, 2-hydroxybenzimidazole, methylenedioxy, dialkoxy, or dialkyl; or (v) hydrogen if $R^9$ and $R^{10}$ taken together are benzo.

Still other PDE4 modulators include, but are not limited to, 7-amido-isoindolyl compounds disclosed in U.S. Pat. No. 7,034,052, which is incorporated herein by reference. Examples include compounds of formula (X22):

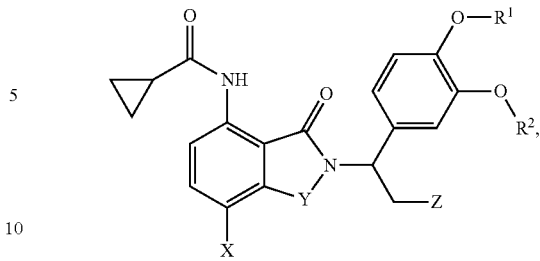

or a pharmaceutically acceptable salt, solvate, hydrate, clathrate, stereoisomer, or prodrug thereof, wherein compounds of formula (X22):

Y is —C(O)—, —CH$_2$, —CH$_2$C(O)— or SO$_2$;

X is H;

Z is (C$_{0-4}$-alkyl)-C(O)R$^3$, C$_{1-4}$-alkyl, (C$_{0-4}$-alkyl)-OH, (C$_{1-4}$-alkyl)-O(C$_{1-4}$-alkyl), (C$_{1-4}$-alkyl)-SO$_2$(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$akyl)$_2$, (C$_{0-4}$-alkyl)-N(H)(OH), or CH$_2$NSO$_2$(C$_{1-4}$-alkyl);

R$_1$ and R$_2$ are independently C$_{1-8}$-alkyl, cycloalkyl, or (C$_{1-4}$-alkyl)cycloalkyl;

$R^3$ is NR$^4$R$^5$, OH, or O—(C$_{1-8}$-alkyl);

$R^4$ is H;

$R^5$ is —OH or —OC(O)R$^6$; and $R^6$ is C$_{1-8}$-alkyl, amino-(C$_{1-8}$-alkyl), (C$_{1-8}$-alkyl)-(C$_{3-6}$-cycloalkyl), C$_{3-6}$-cycloalkyl, phenyl, benzyl, or aryl.

In other embodiments, provided herein is a compound of the following formula (X23):

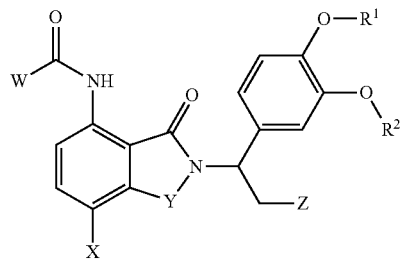

or a pharmaceutically acceptable salt, solvate, hydrate, clathrate, stereoisomer, or prodrug thereof, wherein compounds of formula (X23):

Y is —C(O)—, —CH$_2$, —CH$_2$C(O)—, or SO$_2$;

X is halogen, —CN, —NR$^7$R$^8$, —NO$_2$, or —CF$_3$;

Z is (C$_{0-4}$alkyl)-SO$_2$(C$_{1-4}$-alkyl), —(C$_{0-4}$-alkyl)-CN, —(C$_{0-4}$-alkyl)-C(O)R$^3$, C$_{1-4}$-alkyl, (C$_{0-4}$-alkyl)OH, (C$_{0-4}$-alkyl)O(C$_{1-4}$-alkyl), (C$_{0-4}$-alkyl)SO(C$_{1-4}$-alkyl), (C$_{0-4}$-alkyl)NH$_2$, (C$_{0-4}$-alkyl)N(C$_{1-8}$-alkyl)$_2$, (C$_{0-4}$-alkyl) N(H)(OH), (C$_{0-4}$-alkyl)-dichloropyridine or (C$_{0-4}$-alkyl)NSO$_2$(C$_{1-4}$-alkyl);

W is —C$_{3-6}$-cycloalkyl, —(C$_{1-8}$s-alkyl)-(C$_{3-6}$-cycloalkyl), —(C$_{0-8}$-alkyl)-(C$_{3-6}$-cycloalkyl)NR$_7$R$_8$, (C$_{0-8}$-alkyl)-NR$_7$R$_8$, (C$_{0-4}$alkyl)-CHR$_9$—(C$_{0-4}$alkyl)-NR$_7$R$_8$;

R$^1$ and R$^2$ are independently C$_{1-8}$-alkyl, cycloalkyl, or (C$_{1-4}$-alkyl)cycloalkyl;

$R^3$ is C$_{1-8}$-alkyl, NR$^4$R$^5$, OH, or O—(C$_{1-8}$-alkyl);

$R^4$ and $R^5$ are independently H, C$_{1-8}$-alkyl, (C$_{0-8}$-alkyl)-(C$_{3-6}$-cycloalkyl), OH, or —OC(O)R$^6$;

$R^6$ is C$_{1-8}$-alkyl, (C$_{0-8}$-alkyl)-(C$_{3-6}$-cycloalkyl), amino-(C$_{1-8}$-alkyl), phenyl, benzyl, or aryl;

$R^7$ and $R^8$ are each independently H, $C_{1-8}$-alkyl, $(C_{0-8}$-alkyl)-$(C_{3-6}$-cycloalkyl), phenyl, benzyl, or aryl; or $R^7$ and $R^8$ can be taken together with the atom connecting them to form a 3 to 7 membered heterocycloalkyl or heteroaryl ring;

$R^9$ is $C_{1-4}$ alkyl, $(C_{0-4}$alkyl)aryl, $(C_{0-4}$alkyl)-$(C_{3-6}$-cycloalkyl), $(C_{0-4}$alkyl)-heterocycle.

In one embodiment of the compounds of formula (X23), W is

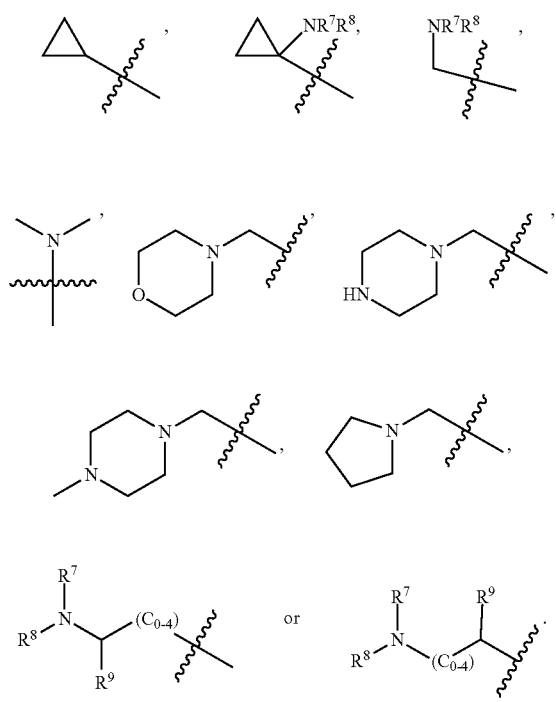

In another embodiment, representative compounds include those of formula (X24):

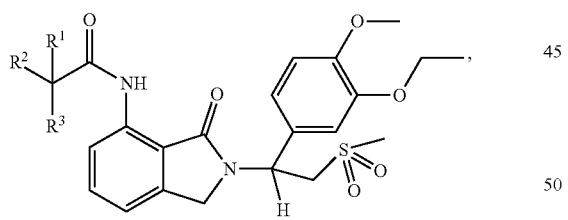

or a pharmaceutically acceptable salt, solvate, hydrate, clathrate, stereoisomer, or prodrug thereof, wherein compounds of formula (X24):

$R^1$, $R^2$, and $R^3$ are independently H or $C_{1-8}$-alkyl, with the proviso that at least one of $R^1$, $R^2$, and $R^3$ is not H.

Still other PDE4 modulators include, but are not limited to, isoindoline compounds disclosed in U.S. publication no. 2006/0025457A1, published Feb. 2, 2006, which is incorporated herein by reference. Representative compounds include those listed in Table 1 below, or a pharmaceutically acceptable salt, solvate, hydrate, clathrate, stereoisomer, or prodrug thereof:

TABLE 1

| No. | Structure |
|---|---|
| 1 | 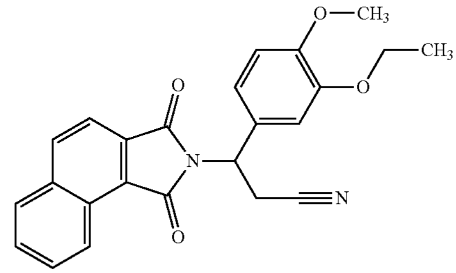 [SMILES: CCOc1cc(C(CC#N)N2C(=O)c3ccc4ccccc4c3C2=O)ccc1OC] |
| 2 | 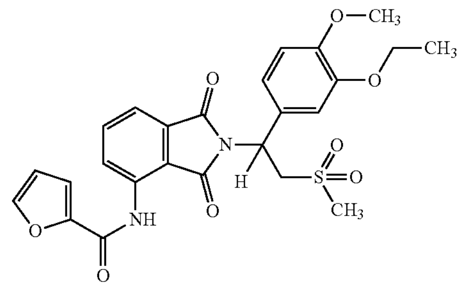 [SMILES: CCOc1cc(C(CS(C)(=O)=O)N2C(=O)c3cccc(NC(=O)c4ccco4)c3C2=O)ccc1OC] |
| 3 | 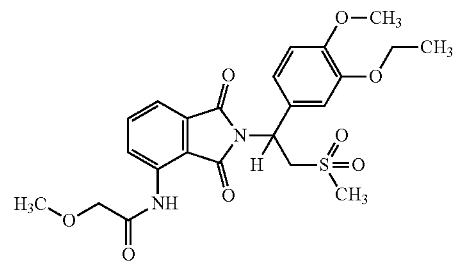 [SMILES: CCOc1cc(C(CS(C)(=O)=O)N2C(=O)c3cccc(NC(=O)COC)c3C2=O)ccc1OC] |
| 4 | 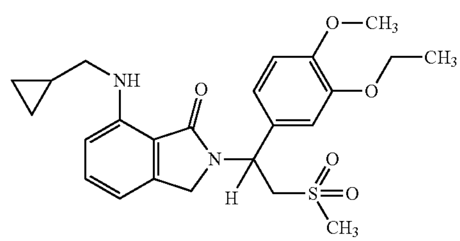 [SMILES: CCOc1cc(C(CS(C)(=O)=O)N2Cc3cccc(NCC4CC4)c3C2=O)ccc1OC] |
| 5 | 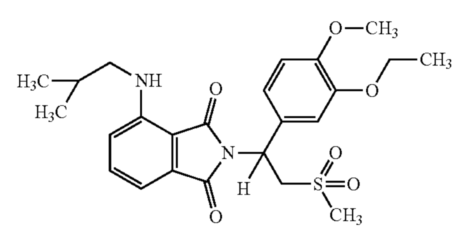 [SMILES: CCOc1cc(C(CS(C)(=O)=O)N2C(=O)c3cccc(NCC(C)C)c3C2=O)ccc1OC] |
| 6 | 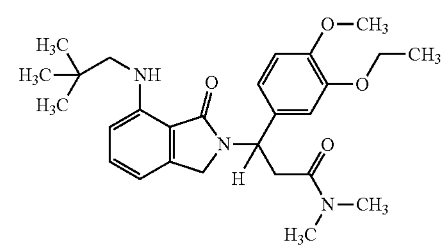 [SMILES: CCOc1cc(C(CC(=O)N(C)C)N2Cc3cccc(NCC(C)(C)C)c3C2=O)ccc1OC] |

TABLE 1-continued

| No. | Structure |
|-----|-----------|
| 7 | 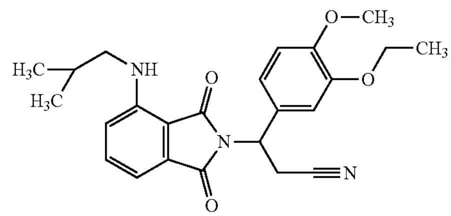 [SMILES: CCOc1cc(C(CC#N)N2C(=O)c3cccc(NCC(C)C)c3C2=O)ccc1OC] |
| 8 | 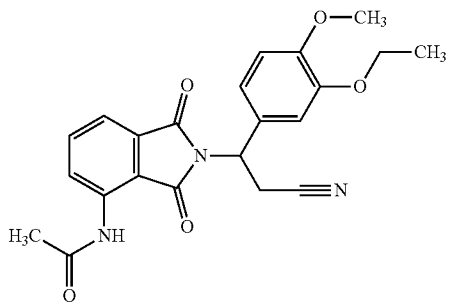 [SMILES: CCOc1cc(C(CC#N)N2C(=O)c3cccc(NC(C)=O)c3C2=O)ccc1OC] |
| 9 | 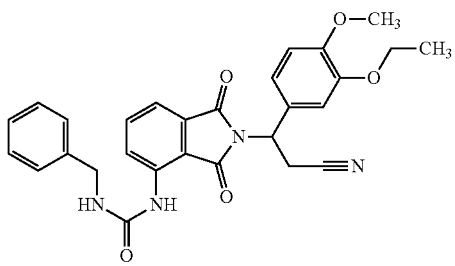 [SMILES: CCOc1cc(C(CC#N)N2C(=O)c3cccc(NC(=O)NCc4ccccc4)c3C2=O)ccc1OC] |
| 10 | 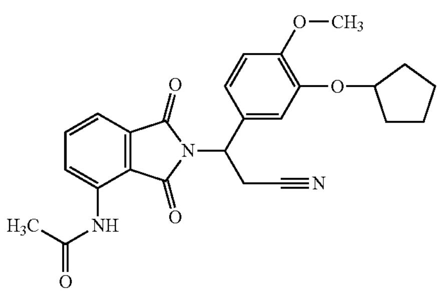 [SMILES: COc1ccc(C(CC#N)N2C(=O)c3cccc(NC(C)=O)c3C2=O)cc1OC1CCCC1] |
| 11 | 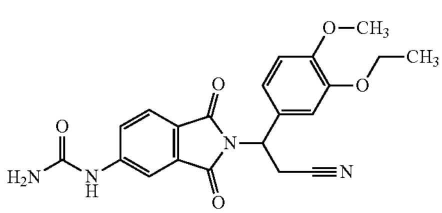 [SMILES: CCOc1cc(C(CC#N)N2C(=O)c3ccc(NC(N)=O)cc3C2=O)ccc1OC] |
| 12 | 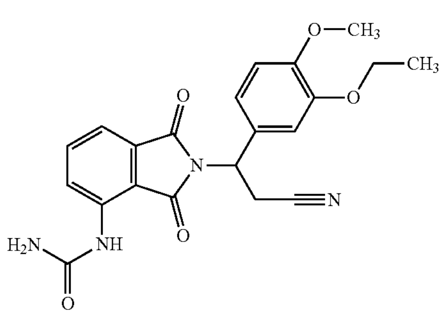 |

TABLE 1-continued

| No. | Structure |
|-----|-----------|
| 13 | 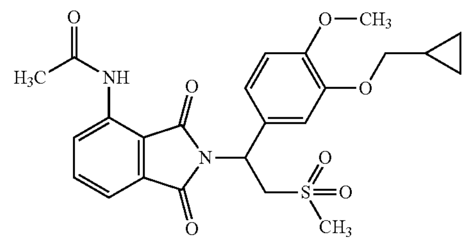 [SMILES: COc1ccc(C(CS(C)(=O)=O)N2C(=O)c3cccc(NC(C)=O)c3C2=O)cc1OCC1CC1] |
| 14 | 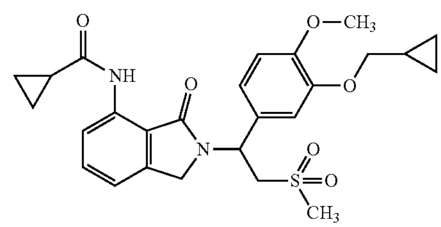 [SMILES: COc1ccc(C(CS(C)(=O)=O)N2Cc3cccc(NC(=O)C4CC4)c3C2=O)cc1OCC1CC1] |
| 15 | 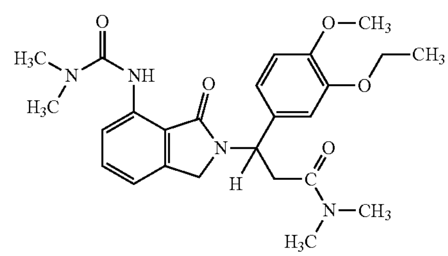 [SMILES: CCOc1cc(C(CC(=O)N(C)C)N2Cc3cccc(NC(=O)N(C)C)c3C2=O)ccc1OC] |
| 16 | 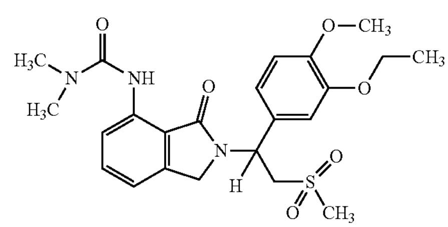 [SMILES: CCOc1cc(C(CS(C)(=O)=O)N2Cc3cccc(NC(=O)N(C)C)c3C2=O)ccc1OC] |

In another embodiment, also provided herein are 2-[1-(3-ethoxy-4-methoxyphenyl)-2-methylsulfonylethyl]-4,5-dinitroisoindoline-1,3-dione, or a pharmaceutically acceptable salt, solvate, hydrate, clathrate, stereoisomer, or prodrug thereof. In one embodiment, provided herein is a hydrochloride salt of 2-[1-(3-ethoxy-4-methoxyphenyl)-2-methylsulfonylethyl]-4,5-dinitroisoindoline-1,3-dione.

Still other PDE4 modulators include, but are not limited to, isoindoline compounds disclosed in U.S. Pat. No. 7,244,259, which is incorporated herein by reference. Representative compounds include cyclopropanecarboxylic acid {2-[1-(3-ethoxy-4-methoxy-phenyl)-2-[1,3,4]oxadiazol-2-yl-ethyl]-3-oxo-2,3-dihydro-1H-isoindol-4-yl}-amide, which has the following chemical structure, or a pharmaceutically acceptable salt, solvate, hydrate, clathrate, stereoisomer, or prodrug thereof:

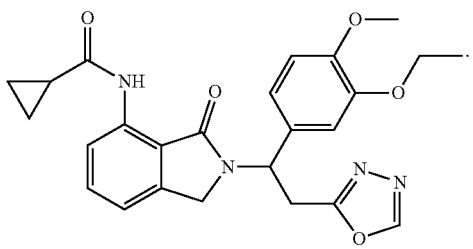 [SMILES: CCOc1cc(C(Cc2nnco2)N2Cc3cccc(NC(=O)C4CC4)c3C2=O)ccc1OC]

Still other PDE4 modulators include, but are not limited to, N-alkyl-hydroxamic acid-isoindolyl compounds disclosed in U.S. Pat. No. 6,911,464, which is incorporated herein by reference. Representative compounds include those of formula (X25):

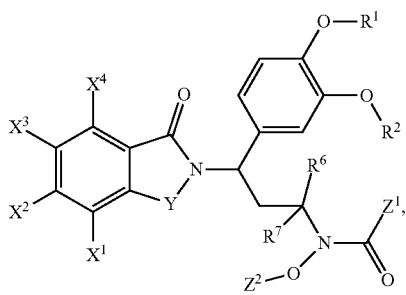

or a pharmaceutically acceptable salt, solvate, hydrate, clathrate, stereoisomer, or prodrug thereof, wherein compounds of formula (X25):

Y is —C(O)—, —CH$_2$, —CH$_2$C(O)— or SO$_2$;

$R^1$ and $R^2$ are independently C$_{1-8}$-alkyl, CF$_2$H, CF$_3$, CH$_2$CHF$_2$, cycloalkyl, or (C$_{1-8}$-alkyl)cycloalkyl;

$Z^1$ is H, C$_{1-6}$-alkyl, —NH$_2$—NR$^3$R$^4$ or OR$^5$;

$Z^2$ is H or C(O)R$^5$;

$X^1$, $X^2$, $X^3$ and $X^4$ are each independently H, halogen, NO$_2$, OR$_3$, CF$_3$, C$_{1-6}$-alkyl, (C$_{0-4}$alkyl)-(C$_{3-6}$-cycloalkyl), (C$_{0-4}$-alkyl)-N—(R$^8$R$^9$), (C$_{0-4}$-alkyl)-NHC(O)—(R$^8$), (C$_{0-4}$-alkyl)-NHC(O)CH(R$^8$)(R$^9$), (C$_{0-4}$-alkyl)-NHC(O)N(R$^8$R$^9$), (C$_{0-4}$-alkyl)-NHC(O)O(R$^8$), (C$_{0-4}$-alkyl)-O—R$_8$, (C$_{0-4}$-alkyl)-imidazolyl, (C$_{0-4}$-alkyl)-pyrrolyl, (C$_{0-4}$-alkyl) oxadiazolyl, (C$_{0-4}$-alkyl)-triazolyl or (C$_{0-4}$-alkyl)-heterocycle;

$R^3$, $R^4$, and $R^5$ are each independently H, C$_{1-6}$-alkyl, O—C$_{1-6}$-alkyl, phenyl, benzyl, or aryl;

$R^6$ and $R^7$ are independently H or C$_{1-6}$-alkyl; and $R^8$ and $R^9$ are each independently H, C$_{1-9}$-alkyl, C$_{3-6}$-cycloalkyl, (C$_{1-6}$-alkyl)-(C$_{3-6}$ cycloalkyl), (C$_{0-6}$-alkyl)-N (R$^4$R$^5$), (C$_{1-6}$-alkyl)-OR$^5$, phenyl, benzyl, aryl, piperidinyl, piperizinyl, pyrolidinyl, morpholino, or C$_{3-7}$-heterocloalkyl.

Still other PDE4 modulators include, but are not limited to, diphenylethylene compounds disclosed in U.S. Pat. No. 7,312,241, which is incorporated herein by reference. Representative compounds include those of formula (X26):

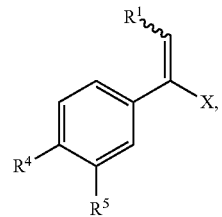

or a pharmaceutically acceptable salt, solvate, hydrate, clathrate, stereoisomer, or prodrug thereof, wherein compounds of formula (X26):

$R^1$ is —CN, lower alkyl, —COOH, —C(O)—N(R$_9$)$_2$, —C(O)-lower alkyl, —C(O)-benzyl, —C(O)O-lower alkyl, —C(O)O-benzyl;

$R^4$ is —H, —NO$_2$, cyano, substituted or unsubstituted lower alkyl, substituted or unsubstituted alkoxy, halogen, —OH, —C(O)(R$_{10}$)$_2$, —COOH, —NH$_2$, or —OC(O)—N(R$_{10}$)$_2$;

$R^5$ is substituted or unsubstituted lower alkyl, substituted or unsubstituted alkoxy, or substituted or unsubstituted alkenyl;

X is substituted or unsubstituted phenyl, substituted or unsubstituted pyridine, substituted or unsubstituted pyrrolidine, substituted or unsubstituted imidizole, substituted or unsubstituted naphthalene, substituted or unsubstituted thiophene, or substituted or unsubstituted cycloalkyl;

each occurrence of $R^9$ is independently —H or substituted or unsubstituted lower alkyl; and each occurrence of $R^{10}$ is independently —H or substituted or unsubstituted lower alkyl.

In another embodiment, representative compounds include those of formula (X27):

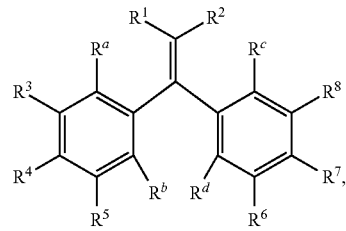

or a pharmaceutically acceptable salt, solvate, hydrate, clathrate, stereoisomer, or prodrug thereof, wherein compounds of formula (X27):

$R^1$ and $R^2$ are independently —H, —CN, substituted or unsubstituted lower alkyl, substituted or unsubstituted alkenyl, substituted or unsubstituted alkynyl, —COOH, —C(O)-lower alkyl, —C(O)O-lower alkyl, —C(O)—N(R$_9$)$_2$, substituted or unsubstituted aryl, or substituted or unsubstituted heterocycle;

each occurrence of $R^a$, $R^b$, $R^c$ and $R^d$ is independently —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO$_2$, —OH, —OPO(OH)$_2$, —N(R$^9$)$_2$, —OC(O)—R$^{10}$, —OC(O)—R$^{10}$—N(R$^{10}$)$_2$, —C(O)N(R$^{10}$)$_2$, —NHC(O)—R$^{10}$, —NHS(O)$_2$—R$^{10}$, —S(O)$_2$—R$^{10}$, —NHC(O)NH—R$^{10}$, —NHC(O)N(R$^{10}$)$_2$, —NHC(O)NHSO$_2$—R$^{10}$, —NHC(O)—R$^{10}$—N(R$^{10}$)$_2$, —NHC(O)CH(R$^{10}$)(N(R$^9$)$_2$) or —NHC(O)—R$^{10}$—NH$_2$;

R³ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R⁹)₂, —OC(O)—R¹⁰, —OC(O)—R¹⁰—N(R¹⁰)₂, —C(O)N(R¹⁰)₂, —NHC(O)—R¹⁰, —NHS(O)₂—R¹⁰, —S(O)₂—R¹⁰, —NHC(O)NH—R¹⁰, —NHC(O)N(R¹⁰)₂, —NHC(O)NHSO₂—R¹⁰, —NHC(O)—R—N(R¹⁰)₂, —NHC(O)CH(R¹⁰)(N(R⁹)₂) or —NHC(O)—R¹⁰—NH₂; or R³ with either Rᵃ or with R⁴, together form —O—C(R¹⁶R¹⁷)—O— or —O—(C(R¹⁶R¹⁷))₂—O—;

R⁴ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R⁹)₂, —OC(O)—R¹⁰, —OC(O)—R¹⁰—N(R¹⁰)₂, —C(O)N(R¹⁰)₂, —NHC(O)—R¹⁰, —NHS(O)₂—R¹⁰, —S(O)₂—R¹⁰, —NHC(O)NH—R¹⁰, —NHC(O)N(R¹⁰)₂, —NHC(O)NHSO₂—R¹⁰, —NHC(O)—R—N(R¹⁰)₂, —NHC(O)CH(R⁰)(N(R⁹)₂) or —NHC(O)—R¹⁰—NH₂;

R⁵ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R⁹)₂, —OC(O)—R¹⁰, —OC(O)—R¹⁰—N(R¹⁰)₂, —C(O)N(R¹⁰)₂, —NHC(O)—R¹⁰, —NHS(O)₂—R¹⁰, —S(O)₂—R¹⁰, —NHC(O)NH—R¹⁰, —NHC(O)N(R¹⁰)₂, —NHC(O)NHSO₂—R¹⁰, —NHC(O)—R—N(R¹⁰)₂, —NHC(O)CH(R¹⁰)(N(R⁹)₂) or —NHC(O)—R¹⁰—NH₂;

R⁶ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R⁹)₂, —OC(O)—R¹⁰, —OC(O)—R¹⁰—N(R¹⁰)₂, —C(O)N(R¹⁰)₂, —NHC(O)—R¹⁰, —NHS(O)₂—R¹⁰, —S(O)₂—R¹⁰, —NHC(O)NH—R¹⁰, —NHC(O)N(R¹⁰)₂, —NHC(O)NHSO₂—R¹⁰, —NHC(O)—R—N(R¹⁰)₂, —NHC(O)CH(R⁰)(N(R⁹)₂) or —NHC(O)—R¹⁰—NH₂;

R⁷ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R⁹)₂, —OC(O)—R¹⁰, —OC(O)—R¹⁰—N(R¹⁰)₂, —C(O)N(R¹⁰)₂, —NHC(O)—R¹⁰, —NHS(O)₂—R¹⁰, —S(O)₂—R¹⁰, —NHC(O)NH—R¹⁰, —NHC(O)N(R¹⁰)₂, —NHC(O)NHSO₂—R¹⁰, —NHC(O)—R—N(R¹⁰)₂, —NHC(O)CH(R¹⁰)(N(R⁹)₂) or —NHC(O)—R¹⁰—NH₂;

R⁸ is —H, substituted or unsubstituted lower alkyl, substituted or unsubstituted aryl, substituted or unsubstituted heterocycle, substituted or unsubstituted cycloalkyl, substituted or unsubstituted alkoxy, halogen, cyano, —NO₂, —OH, —OPO(OH)₂, —N(R⁹)₂, —OC(O)—R¹⁰, —OC(O)—R¹⁰—N(R¹⁰)₂, —C(O)N(R¹⁰)₂, —NHC(O)—R¹⁰, —NHS(O)₂—R¹⁰, —S(O)₂—R¹⁰, —NHC(O)NH—R¹⁰, —NHC(O)N(R¹⁰)₂, —NHC(O)NHSO₂—R¹⁰, —NHC(O)—R—N(R¹⁰)₂, —NHC(O)CH(R⁰)(N(R⁹)₂) or —NHC(O)—R¹⁰—NH₂, or R⁸ with either Rᶜ or with R⁷, together form —O—C(R¹⁶R¹⁷)—O— or —O—(C(R¹⁶R¹⁷))₂—O—;

each occurrence of R⁹ is independently —H, substituted or unsubstituted lower alkyl, or substituted or unsubstituted cycloalkyl;

each occurrence of R¹⁰ is independently substituted or unsubstituted lower alkyl, substituted or unsubstituted cycloalkyl, substituted or unsubstituted aryl, substituted or unsubstituted lower hydroxyalkyl, or R¹⁰ and a nitrogen to which it is attached form a substituted or unsubstituted heterocycle; or R¹⁰ is —H where appropriate; and each occurrence of R¹⁶ and R¹⁷ is independently —H or halogen.

In another embodiment, provided herein is 3-(3,4-dimethoxyphenyl)-3-(1-oxo-1,3-dihydroisoindol-2-yl)propionic acid methyl ester:

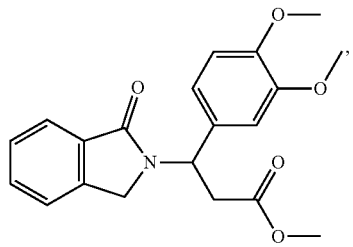 [SMILES: COC(=O)CC(c1ccc(OC)c(OC)c1)N1Cc2ccccc2C1=O]

or a pharmaceutically acceptable salt, solvate, hydrate, clathrate, stereoisomer, or prodrug thereof.

In one embodiment, provided herein are 2-[1-(3-ethoxy-4-methoxyphenyl)-2-methylsulfonylethyl]-4-acetylaminoisoindoline-1,3-dione and cyclopropyl-N-{2-[1-(3-ethoxy-4-methoxyphenyl)-2-(methylsulfonyl)ethyl]-3-oxoisoindolin-4-yl}carboxamide, which respectively have the following structures:

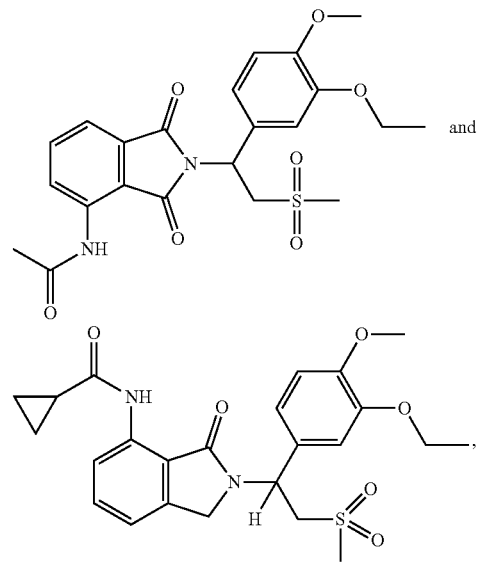

or a pharmaceutically acceptable salt, solvate, hydrate, clathrate, stereoisomer, or prodrug thereof. In another embodiment, stereoisomers of these compounds are also encompassed.

Compounds provided herein can either be commercially purchased or prepared according to the methods described in the patents or patent publications disclosed herein. Further, optically pure compositions can be asymmetrically synthesized or resolved using known resolving agents or chiral columns as well as other standard synthetic organic chemistry techniques.

Various PDE4 modulators contain one or more chiral centers, and can exist as racemic mixtures of enantiomers or mixtures of diastereomers. In one embodiment, provided herein is the use of stereomerically pure forms of such compounds, as well as the use of mixtures of those forms. For example, mixtures comprising equal or unequal amounts of the enantiomers of PDE4 modulators may be used in methods and compositions provided herein. The purified (R) or (S) enantiomers of the specific compounds disclosed herein may be used substantially free of its other enantiomer.

Compounds used herein may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.3 Methods of Treating, Preventing, or Managing Immune Reconstitution Inflammation Syndrome (IRIS)

Provided herein are methods of treating, preventing, or managing IRIS in a patient in need thereof by administering to the patient an effective amount of a PDE4 modulator described herein. In one aspect is a method of treating or managing IRIS in a patient in need thereof by administering an effective amount (e.g., therapeutically effective amount) of a PDE4 modulator described herein. In another aspect is a method of preventing the onset of IRIS in a patient at risk of developing IRIS by administering an effective amount (e.g., a prophylactically effective amount) of a PDE4 modulator described herein. The methods described herein are useful for preventing IRIS before administration of a therapy (e.g., ART) that is likely to induce or cause IRIS. The methods described herein are useful for preventing IRIS after administration of a therapy (e.g., ART) that is likely to induce or cause IRIS. The methods described herein are useful for preventing IRIS following withdrawal of a therapy (e.g., ART) that is likely to induce or cause IRIS.

In one embodiment, the PDE4 modulator for use in the methods of treating, preventing, or managing IRIS as described herein in a patient in need thereof is a compound having formula of Compound A, A1, B, B1, or C as described herein, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is a compound having formula of Compound A, A1, B, B1, or C as described herein. In one embodiment, the PDE4 modulator for use in the methods of treating, preventing, or managing IRIS as described herein in a patient in need thereof is Compound A, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is Compound A.

In one embodiment, the PDE4 modulator for use in the methods of treating, preventing, or managing IRIS as described herein in a patient in need thereof is Compound A1, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is Compound A1.

In one embodiment, the PDE4 modulator for use in the methods of treating, preventing, or managing IRIS as described herein in a patient in need thereof is Compound B, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is Compound B.

In one embodiment, the PDE4 modulator for use in the methods of treating, preventing, or managing IRIS as described herein in a patient in need thereof is Compound B1, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is Compound B1.

In one embodiment, the PDE4 modulator for use in the methods of treating, preventing, or managing IRIS as described herein in a patient in need thereof is Compound C, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is Compound C.

In one embodiment, the PDE4 modulator for use in the methods of treating, preventing, or managing IRIS as described herein in a patient in need thereof is a compound set forth in Table 1, including pharmaceutically acceptable salts, solvates, hydrates, clathrates, and prodrugs thereof. In one embodiment, the PDE4 modulator for use in the methods of treating, preventing, or managing IRIS as described herein in a patient in need thereof is a compound set forth in Table 1.

The methods described herein are applicable to treating, preventing, and managing IRIS in patients having an immunodeficiency resulting from any condition, whether the congenital (e.g., a disease causing an immunodeficiency such as an autoimmune disease) or resultant from an disease which compromises an individual's immune system (e.g., HIV/AIDS).

In one embodiment the patient is an HIV patient. In one embodiment the patient has an immunodeficiency unrelated to HIV. The patient may be at risk of developing IRIS. Risk factors and pathologic conditions for identifying IRIS are known in the art and readily understood by those in art. *Indian J. Med. Res.* (2011) 134(6) 866-877. In certain embodiments, the patient at risk of developing IRIS is a HIV patient who will receive ART as described herein and understood in the art. In certain embodiments, the patient at risk of developing IRIS is a HIV patient who has received ART for the first time. In certain embodiments, the patient at risk of developing IRIS is a HIV patient who is reinitiating ART therapy. In certain embodiments, the patient at risk of developing IRIS is a HIV patient for whom ART is being withdrawn (e.g., end of treatment). In certain embodiments, the patient has an immunodeficiency unrelated to HIV and is at risk of developing IRIS.

In another embodiment, the patient has a disease (e.g., congenital) that causes an immunodeficiency. In one embodiment, such a patient is at risk of developing IRIS. In certain instances, such patients are at risk of developing IRIS as a result of treatment for their immunodeficiency (e.g., initiation, re-initiation, or withdrawal of therapy).

In one embodiment, the patient has a decreased CD4+ count compared to a non-immunodeficient subject. In one embodiment, the decreased CD4+ count is characterized by less than about 10, 15, 25, 30, 40, 50, 60, 70, 80, 90, 100, 125, 150, 200, 250, or 300 cells/µl of sample. In certain embodiments, the patient is an HIV patient and has a CD4+ count of less than about 100 cells/µl of sample.

In certain instances it may be beneficial to measure CD4+ counts following administration of a therapy for immune reconstitution (e.g., ART). In one embodiment, such measurements are taken over the course of such a therapy. When taken over a period of time, measurements of CD4+ count can be performed daily, every other day, weekly, or monthly. Measurements can be compared to a control sample (e.g., a non-immunodeficient subject) or to previous other measurements. Increased CD4+ counts can indicate a risk for the onset of IRIS. In one embodiment, an increase in CD4+ count of ≥10, 12, 14, 16, 18, 20, 22, 25, 27, 30, or more cells/µl can be predictive of the onset of IRIS. Provided herein is a method of determining the presence of IRIS in a HIV patient and thereby when to administer a PDE4 modulator described herein to prevent, treat, or manage IRIS, where the method includes measuring the CD4+ count of a HIV patient, comparing the measurement to a control or one or more other measurements taken from the same patient over a period of time, where an increase of at least 20 cells/µl of sample indicates the onset of or progression of IRIS and that a PDE4 modulator described herein should be administered.

In certain instances it may be beneficial to measure HIV loads (HIV titers) of an HIV patient during and following administration of ART. In one embodiment, measurements of HIV loads are taken over the course of ART. Measurements may be compared to a control sample or to other previous measurements. A rapid or significant decrease in plasma HIV load can indicate a risk for the onset of IRIS. In one embodiment, a decrease in plasma HIV load of ≥0.5, 0.75, 1, 1.25, 1.5, 1.75, 2, 2.25, 2.5, or more $\log_{10}$ can be predictive of the onset of IRIS. The measurement of a decrease in plasma HIV load as described herein can indicate the need or time for administration of a PDE4 modulator described herein to prevent, treat, or manage IRIS in a HIV patient. Provided herein is a method of determining the presence of IRIS in a HIV patient and thereby when to administer a PDE4 modulator described herein to prevent, treat, or manage IRIS, where the method includes measuring the HIV load of a HIV patient, comparing the measurement to a control or one or more other measurements taken from the same patient over a period of time, where a decrease of at least 0.5 $\log_{10}$ of plasma HIV load indicates the onset of or progression of IRIS and that a PDE4 modulator described herein should be administered.

In certain embodiments, IRIS is caused by a latent infection in the patient. In such instances, the latent infection is masked by the patient's weakened immune system. In one embodiment, the latent infection is "clinically silent" (e.g., the patient presents no or few symptoms of infection).

In other embodiments, IRIS is characterized by or results from an opportunistic infection. In one embodiment, the opportunistic infection is a latent infection as described herein in the patient prior to any immune reconstitution. In one embodiment, the opportunistic infection is acquired before immune reconstitution. In one embodiment, the opportunistic infection is acquired before or during administration of a therapy for immune reconstitution (e.g., ART). The IRIS can be characterized by or results from an opportunistic bacterial infection. The IRIS can be characterized by or result from an opportunistic parasitic infection. In one embodiment, IRIS is characterized by or results from a parasitic infection (e.g., opportunistic), where the parasitic infection is characterized by or caused by Kala Azar or falcipaum malarial infection.

In one embodiment, IRIS is characterized by or results from cytomegalovirus (CMV), CMV retinitis, *crytoccocal meningitis, croyptococcosis*, eosinophilic folliculitis, hepatitis B, hepatitis C, herpes virus, herpes simplex virus (HSV), varicella zoster virus (shingles), human pampillomavirus (HPV), karposi sarcoma (HHV8), *Mycobacterium avium* complex (MAC), *Pneumocystis* jiroveci pneumonia (PCP), progressive multifocal leukoencephalopathy (PML), or *Mycobacterium tuberculosis* (TB) infection. In one embodiment, IRIS is characterized by or results from cytomegalovirus (CMV). In one embodiment, IRIS is characterized or caused by CMV retinitis. In one embodiment, IRIS is characterized by or results from *crytoccocal meningitis*. In one embodiment, IRIS is characterized by or results from *croyptococcosis*. In one embodiment, IRIS is characterized by or results from eosinophilic folliculitis. In one embodiment, IRIS is characterized by or results from hepatitis B. In one embodiment, IRIS is characterized by or results from hepatitis C. In one embodiment, IRIS is characterized by or results from herpes virus. In one embodiment, IRIS is characterized by or results from herpes simplex virus (HSV). In one embodiment, IRIS is characterized by or results from varicella zoster virus (shingles). In one embodiment, IRIS is characterized by or results from human pampillomavirus (HPV). In one embodiment, IRIS is characterized by or results from karposi sarcoma (HHV8). In one embodiment, IRIS is characterized by or results from *Mycobacterium avium* complex (MAC). In one embodiment, IRIS is characterized by or results from *Pneumocystis jiroveci* pneumonia (PCP.) In one embodiment, IRIS is characterized by or results from progressive multifocal leukoencephalopathy (PML). In a particular embodiment, IRIS is characterized by or results from *Mycobacterium tuberculosis* (TB).

Provided herein are methods of treating or managing IRIS in a HIV patient described herein by administering an effective amount of a PDE4 modulator described herein to the patient. The administration of a PDE4 modulator described herein can occur after administration of ART to a HIV patient described herein. The administration of a PDE4 modulator described herein can occur after withdrawal of ART to a HIV patient described herein.

Further provided herein are methods of preventing IRIS in a HIV patient described herein by administering an effective amount of a PDE4 modulator described herein to the patient. The administration of a PDE4 modulator described herein can occur before administration of ART to a HIV patient described herein. The administration of a PDE4 modulator described herein can occur before withdrawal of ART to a HIV patient described herein.

PDE4 modulators useful in the methods described herein include those set forth herein in Section 4.2. In certain embodiments, the PDE4 modulator is a compound having formula of Compound A, A1, B, B1, or C as described herein, including pharmaceutically acceptable salts, solvates, hydrates, clathrates, and prodrugs thereof. In certain embodiments, the PDE4 modulator is a compound having formula of Compound A or A1 as described herein, including pharmaceutically acceptable salts, solvates, hydrates, clathrates, and prodrugs thereof. In certain embodiments, the PDE4 modulator is a compound having formula of Compound B or B1 as described herein, including pharmaceutically acceptable salts, solvates, hydrates, clathrates, and prodrugs thereof. In certain embodiments, the PDE4 modulator is a compound set forth in Table 1, including pharmaceutically acceptable salts, solvates, hydrates, clathrates, and prodrugs thereof.

PDE4 modulators useful in the methods described herein can be administered orally as described herein and in forms as provided herein. In one embodiment, a PDE4 modulator described herein is administered orally in a tablet, capsule, or satchet form to a patient described herein. In one embodiment, the PDE4 modulator is a Compound of A, A1, B, B1, C, or a compound as set forth in Table 1, including pharmaceutically acceptable salts, solvates, hydrates, clathrates, and prodrugs thereof and is administered orally. In one embodiment, the PDE4 modulator is Compound A or A1, including pharmaceutically acceptable salts, solvates, hydrates, clathrates, and prodrugs thereof and is administered orally. In one embodiment, the PDE4 modulator is Compound B or B1, including pharmaceutically acceptable salts, solvates, hydrates, clathrates, and prodrugs thereof and is administered orally. In one embodiment, the PDE4 modulator is Compound C, including pharmaceutically acceptable salts, solvates, hydrates, clathrates, and prodrugs thereof and is administered orally. In one embodiment, the PDE4 modulator is a compound set forth in Table 1, including pharmaceutically acceptable salts, solvates, hydrates, clathrates, and prodrugs thereof and is administered orally. In certain instances, PDE4 modulators useful in the methods described herein are provided in pharmaceutical compositions as provided herein.

In another aspect provided herein is a method for treating or managing IRIS in a patient described herein who is in need of such therapy by administering a PDE4 modulator described herein in combination with a second active agent described herein. In certain embodiments, the second active agent is a NSAID or corticosteroid described herein in Section 4.4.

In still another aspect is a method for preventing IRIS in a patient described herein who is in need of such therapy by administering a PDE4 modulator described herein in combination with a second active agent described herein. In certain embodiments, the second active agent is a NSAID or corticosteroid described herein in Section 4.4.

Also provided herein are methods of treating an opportunistic infection and IRIS by administering an effective amount of PDE4 modulator described herein. In one embodiment, the method includes simultaneously treating *Mycobacterium tuberculosis* and IRIS by administering a PDE4 modulator described herein. In such instances, the PDE4 modulator can be co-administered with an anti-tuberculosis agent, such as for example, isoniazid, rifampin, pyrazinamide, streptomycin, ethambutol, capreomycin, ethionamide, cycloserine, levafloxacin, ciprofloxacin, amikacin, moxifloxicin, p-aminosalicylic acid, kanamycin, viomycin, enciomycin, protionamide, rifabutin, clarithromycin, linezolid, thioacetazone, arginine, vitamin B, and corticosteroids. In such methods the patient is as described herein and, in certain instance, is a HIV patient described herein.

4.4 Combination Therapy

PDE4 modulators described herein can be used with or combined with other pharmacologically active compounds ("second active agents or ingredients") in the methods herein. Without being bound by any particular theory, certain combinations of second active agents and PDE4 modulators described herein work synergistically in the methods provided herein. PDE4 modulators can also work to alleviate adverse effects associated with certain second active agents, and some second active agents can be used to alleviate adverse effects associated with PDE4 modulators provided herein.

One or more second active ingredients or agents can be used in the methods and compositions provided herein together with a PDE4 modulator. Second active agents can be large molecules (e.g., proteins and antibodies) or small molecules (e.g., synthetic inorganic, organometallic, or organic molecules).

In certain embodiment, the PDE4 modulator, or a pharmaceutically acceptable salt, solvate (e.g., hydrate), stereoisomer, clathrate, or prodrug thereof, in combination with one or more second active agents such as those disclosed herein and/or in combination with other medical procedures such as those disclosed herein.

Administration of a PDE4 modulator provided herein and at least one second active agent to a patient can occur simultaneously or sequentially by the same or different routes of administration. The suitability of a particular route of administration employed for a particular second active agent will depend on the second active agent itself (e.g., whether it can be administered topically or orally without decomposition prior to entering the blood stream) and the disease being treated. A particular route of administration for a PDE4 modulator provided herein is oral or topical administration. Particular routes of administration for the second active agents or ingredients of the invention are known to those of ordinary skill in the art. See, e.g., *The Merck Manual*, 430-431 (17$^{th}$ ed., 1999).

The amount of second active agent administered can be determined based on the specific agent used, the type of disease being treated or managed, the severity and stage of disease and the amount(s) of the compounds of the invention and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* (56$^{th}$ Ed., 2004). Further, the amounts and methods of administration of the second active agents disclosed herein for the treatment, prevention and/or management of opportunistic infections, such as *mycobacterium tuberculosis*, and for HIV are disclosed in the literature, e.g., *Physician's Desk Reference* (56$^{th}$ Ed., 2004), which is incorporated herein by reference. It is further contemplated that combination therapies described herein include administration of a PDE4 modulator while a patient is currently undergoing administration of ART.

In some embodiments, the combination therapies provided herein include, but are not limited to, the combination of a PDE4 modulator as disclosed herein, e.g., Compound A, Compound A1, Compound B, Compound B1, Compound C, a compound as set forth in Table 1, or a pharmaceutically acceptable salt, stereoisomer, solvate, hydrate, clathrate, or prodrug thereof, with one or more steroids or anti-inflammatory agents.

In some embodiments of interest, the second active agents may include, but are not limited to, anti-inflammatory agents such as, but not limited to, acetaminophen (e.g., TYLENOL®), 5-aminosalicylic acid derivatives, salicylates, corticosteroids and nonsteroidal anti-inflammatory drugs. A non-limiting example of 5-aminosalicylic acid derivatives is sulfasalazine (e.g., AZULFIDINE®). A non-limiting examples of salicylates is acetylsalicylic acid (e.g., ASPIRIN®).

Non-limiting examples of corticosteroids include dexamethasone (e.g., AZIUM® or VOREN®), hydrocortisone (e.g., CETACORT®, HYTONE® or NUTRACORT®), beclomethasone (e.g., VANCERIL®), budesonide (e.g., PULMICORT®), fluticasone (e.g., FLONASE® or FLOVENT®), methylprednisolone (e.g., DEPO-MEDROL®, SOLU-MEDROL® or MEDROL®), mometasone furoate (e.g., NASONE® or ELOCON®), prednisone (e.g., DELTASON®, ORASON®, PREDNICEN-M® or LIQUID PRED®) and triamcinolone (e.g., AZMACORT®).

Non-limiting examples of nonsteroidal anti-inflammatory drugs include celecoxib (CELEBREX®), diclofenac (e.g., ARTHROTEC®), diflunisal (e.g., DOLOBID®), etodolac (e.g., LODINE®), fenoprofen (e.g., NALFON®), flurbiprofen (e.g., ANSAID®), ibuprofen (e.g., ADVIL®, CHILDREN'S ADVIL/MOTRIN®, MEDIPREN®, MOTRIN®, NUPRIN® or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), mefenamic acid (e.g., PONSTEL®), meloxicam (e.g., MOBIC®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), tolmetin (e.g., TOLECTIN® DS or TOLECTIN®).

In other embodiments, the second active agent is an agent useful for treating an opportunistic infection (e.g., a bacterial, yeast, fungal, parasitic, or viral infection).

Useful anti-bacterial agents in the methods described herein include, but are not limited to, agents from all known anti-microbial classes such as, for example:

penicillins such as penicillin, amoxicillin, ampicillin, azlocillin, mezlocillin, piperacillin, carboxypenicillin, carbenicillin, ticarcillin, cloxacillin, dicloxacillin, methicillin, nafcillin, oxacillin, or mecillinam;

beta-lactam inhibitors such as amoxicillin-clavulanic acid, ampicillin-sulbactam, aztreonam-avibactam, ceftaroline-avibactam, ceftazidime-avibactam, ceftolozane-tazobactam, piperacillin-tazobactam or ticarcillin-clavulanic acid;

cephems (e.g. cephalosporins) such as cefazolin, cephalothin, cephapirin, cephradine, cefoperazone, cefotaxime, ceftazidime, ceftizoxime, ceftriaxone, cefepime, ceftaroline, ceftobiprole, cefmetazole, cefotetan, cefoxitin, moxalactam, cefaclor, cefadroxil, cefdinir, cefditoren, cefetamet, cefixime, cefpodoxime, cefprozil, ceftibuten, cefuroxime (oral), cephalexin, cephradine, or loracarbef;

penems such as biapenem, doripenem, ertapenem, imipenem, meropenem, razupenem, faropenem, or sulopenem;

aminocyclitols, aminoglycosides, and ansamycins such as spectinomycin, amikacin, gentamicin, kanamycin, netilmicin, plazomicin, streptomycin, tobramycin, and rifampin;

folate pathway inhibitors and fosfomycins such as iclaprim, sulfonamides, trimethoprim, trimethoprim-sulfamethoxazole, and fosfomycin;

glycopeptides such as vancomycin, dalbavancin, oritavancin, ramoplanin, teicoplanin, and telavancin;

lincosamides, lipopeptides, and macrocyclics such as clindamycin, daptomycin, surotomycin, colistin, polymyxin B, and fidaxomycin;

macrolides such as azithromycin, clarithromycin, dirithromycin, erythromycin, telithromycin, and solithromycin;

nitrofurans, nitroimidazoles, oxazolidinones, and thiazolides such as nitrofurantoin, metronidazole, tinidazole, linezolid, tedizolid, nitazoxanide, and tizoxanide;

phenicols, pseudomonic acids, and steroidal such as chloramphenicol, mupirocin, and fusidic acid;

quinolones such as cinoxacin, garenoxacin, nalidixic acid, besifloxacin, ciprofloxacin, clinafloxacin, enoxacin, finafloxacin, fleroxacin, gatifloxacin, gemifloxacin, grepafloxacin, levofloxacin, lomefloxacin, moxifloxacin, norfloxacin, ofloxacin, sparfloxacin, trovafloxacin, and urifloxacin (purlifloxacin);

streptogramins such as linopristin-flopristin and quinupristin-dalfopristin; and tetracyclines such as doxycycline, ervacycline, minocycline, tetracycline, tigecycline, omadacycline.

Useful anti-fungal and anti-yeast agents in the methods described herein include, but are not limited to, agents from all known anti-fungal classes such as, for example:

polyenes such as nystatin, amphotericin B, flucytosine, candicidin, filipin, hamycin, natamycin and rimocidin;

azoles (imidazoles, triazoles, and thiazoles) such as bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, and abafungin;

echinocandins such as caspofungin, anidulafungin, and micafungin; and allylamines such as naftifine, terbinafine, butenafine, and amorolfin.

In still other embodiments, the second active agent an anti-tuberculosis agent for treating *Mycobacterium tuberculosis* infection. Exemplary anti-tuberculosis agents include, but are not limited to, isoniazid, rifampin, pyrazinamide, streptomycin, ethambutol, capreomycin, ethionamide, cycloserine, levofloxacin, ciprofloxacin, amikacin, moxifloxicin, p-aminosalicylic acid, kanamycin, viomycin, enciomycin, protionamide, rifabutin, clarithromycin, linezolid, thioacetazone, arginine, vitamin B, and corticosteroids such as those described herein.

In yet another embodiment, the second active agent is an anti-malarial drug for treating malaria infection. Exemplary anti-malarial drugs include, but are not limited to, quinine, quinidine, tetracycline, chloroquine, doxycycline, mefloquine, clindamycin, atovaquone, proguanil, primaquine, pyrimethamine, amodiaquine, sulfonamides, artemisinin, artemether, and lumefantrine.

4.5 Dosages

In one embodiment, a PDE4 modulator provided herein can be administered orally and daily in an amount of from about 1 to about 1000 mg, from about 1 to about 500 mg, from about 1 to about 250 mg, from about 1 to about 150 mg, from about 0.1 to about 500 mg, from about 0.1 to about 250 mg, from about 0.1 to about 200 mg, from about 0.1 to about 150 mg, from about 1 to about 50 mg, or from about 2 to about 25 mg. In one embodiment, a PDE4 modulator described herein can be administered in an amount of about:

10 mg to about 200 mg; 10 mg to about 100 mg; 10 mg to about 50 mg; 10 mg to about 40 mg; 20 mg to about 100 mg; or 20 mg to about 40 mg. In certain embodiments, a PDE4 modulator described herein is administered in an amount of about: 10 mg, 20 mg, 30 mg, 40 mg, 50 mg, 60 mg, 70 mg, 80 mg, 90 mg, or 100 mg (PO or BID).

In certain embodiments, the amount of a PDE4 modulator administered prophylactically to a patient described herein is greater than a dosage administered therapeutically. In other embodiments, the dosage of a PDE4 modulator described herein is adjusted (e.g., increased) depending on the severity of the IRIS. In such instances, a greater dose can provide a greater or faster therapeutic benefit to the patient. In one embodiment a PDE4 modulator described herein can be administered in high enough concentrations to inhibit expression of GM-CSF, IL-1β, RANTES, or IL8. PDE4 modulators described herein can be administered in effective amounts until resolution of IRIS or until the occurrence of an adverse effect associated with the administration of the PDE4 modulator to a patient.

In one embodiment, one or more PDE4 modulators provided herein are administered to a patient described herein prior to, during, or after the onset of IRIS. In such instances, the one or more PDE4 modulators can be administered in the same amount or varied amounts as described herein. The one or more PDE4 modulators can also be co-administered with a second active agent as described herein.

4.6 Pharmaceutical Compositions and Dosage Forms

Pharmaceutical compositions can be used in the preparation of individual, single unit dosage forms. Pharmaceutical compositions and dosage forms provided herein may comprise a PDE4 modulator, including but not limited to Compound A, Compound A1, Compound B, Compound B1, Compound C, or a pharmaceutically acceptable salt, stereoisomer, solvate, hydrate, clathrate, or prodrug thereof. Pharmaceutical compositions and dosage forms may further comprise one or more carriers, excipients, or diluents.

Single unit dosage forms provided herein are suitable for oral, mucosal (e.g., nasal, sublingual, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms provided herein will vary from one another will be readily apparent to those skilled in the art. See, e.g., *Remington's Pharmaceutical Sciences*, 20th ed., Mack Publishing, Easton Pa. (2000).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein may comprise excipients that are well known in the art and are listed, for example, in the *U.S. Pharmacopeia* (USP) 25-NF20 (2002). In general, lactose-free compositions comprise active ingredients, a binder/filler and a lubricant in pharmaceutically compatible and pharmaceutically acceptable amounts. Particular lactose-free dosage forms comprise active ingredients, microcrystalline cellulose, pre-gelatinized starch and magnesium stearate.

Also provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein may be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical dosage forms provided herein comprise either one of (S)—N-(2-(1-(3-ethoxy-4-methoxyphenyl)-2-(methylsulfonyl)ethyl)-1,3-dioxoisoindolin-4-yl)acetamide or (S)—N-(2-(1-(3-ethoxy-4-methoxyphenyl)-2-(methylsulfonyl)ethyl)-3-oxoisoindolin-4-yl)cyclopropanecarboxamide, or a pharmaceutically acceptable salt or solvate thereof in an amount of from about 1 to about 1,000 mg. Typical dosage forms comprise one of Compound A, Compound A1, Compound B, Compound B1, Compound C, or a pharmaceutically acceptable salt, stereoisomer, or solvate thereof in an amount of about 1, 2, 5, 7.5, 10, 12.5, 15, 17.5, 20, 25, 30, 50, 100, 150 or 200 mg. In a particular embodiment, a dosage form comprises one of Compound A, Compound A1, Compound B, Compound B1, or Compound C, in an amount of about 1, 5, 10, 15, 20, 25, 30, 50, 100 or 200 mg.

The magnitude of a therapeutic dose of a particular PDE4 modulator in the treatment of IRIS will vary, however, with the nature and severity of IRIS, and the route by which the active ingredient is administered. The dose, and perhaps the dose frequency, will also vary according to the age, body weight, and response of the individual subject. Suitable dosing regimens can be readily selected by those skilled in the art with due consideration of such factors.

In general, the recommended daily dose ranges described herein lie within the range of from about 0.1 mg to about 1,000 mg per day, given as a single once-a-day dose or as divided doses throughout a day. More specifically, the daily dose may be administered once, twice, three times, or four times daily in equally divided doses. Specifically, a daily dose range may be from about 1 mg to about 500 mg per day, more specifically, between about 10 mg and about 200 mg per day. In one embodiment, the daily dosage range is between about 10 mg and about 100 mg per day. Specifically, the daily dose may be administered in 1 mg, 5 mg, 6.25 mg, 10 mg, 15 mg, 20 mg, 25 mg, 30 mg, 50 mg, 100 mg, 200 mg, 300 mg, 400 mg or 500 mg dosage forms (Q.D. or B.I.D.). In one embodiment, the daily dosage can be administered in an amount of about 10 mg, 20 mg, 30 mg, 40 mg, 50 mg, 60 mg, 70 mg, 80 mg, 90 mg, or 100 mg as a single dose or divided dose (e.g. twice daily) to a patient described herein. In certain embodiments, PDE4 modulator is a compound of Compound A or A1 and is administered in an amount of about 10 mg to about 100 mg per day. In certain embodiments, the PDE4 modulator is Compound A or A1 and is administered in an amount of about 60 mg. In one embodiment, the PDE4 modulator is Compound A or A1 and is administered as a twice daily dosage of about 30 mg per dose. In one embodiment, the PDE4 modulator is Compound A or A1 and is administered as a single dosage of about 40 mg per day. In managing the subject, the therapy may be initiated at a lower dose, perhaps about 1 mg to about 25 mg, and increased if necessary up to about 200 mg to about 1,000 mg per day as either a single dose or divided doses, depending on the subject's global response.

In certain embodiments, a PDE4 modulator as described herein can be administered using a titration schedule. For example, a patient described herein can be administered a low amount of a PDE4 modulator described herein (e.g. about 10 mg) as a single daily dose which can be titrated to greater amounts or administered at greater frequency. Such titrations are provided in, for example, U.S. Patent Publication No. US 2014/0301980, which is herein incorporated by reference in its entirety for all purposes. Thus, in one embodiment, Compound A, A1, B, B1, or C can be administered according to the following titration schedule:

(i) 10 mg in the morning on the first day of administration;

(ii) 10 mg in the morning and 10 mg after noon on the second day of administration;

(iii) 10 mg in the morning and 20 mg after noon on the third day of administration;

(iv) 20 mg in the morning and 20 mg after noon on the fourth day of administration;

(v) 20 mg in the morning and 30 mg after noon on the fifth day of administration; and (vi) 30 mg in the morning and 30 mg after noon on the sixth and every subsequent day of administration.

In further embodiments, the daily dose of Compound A, Compound A1, Compound B, Compound B1, or Compound C is from about 0.01 mg to about 100 mg per kg of a body weight of a subject. In some embodiments, the daily dose of the chosen compound is about 1 mg/kg, 5 mg/kg, 6.25 mg/kg, 10 mg/kg or 25 mg/kg. In certain embodiments, the therapeutically effective amount of the first active agent as provided herein is about 1, 5, or 25 mg per kg of a body weight of the subject per day and the therapeutically effective amount of the additional active agent as provided herein is about 1, 5, or 6.25 mg per kg of a body weight of the subject per day.

4.6.1 Oral Dosage Forms

Pharmaceutical compositions provided herein that are suitable for oral administration can be presented as discrete dosage forms, such as, but not limited to, tablets (e.g., chewable tablets), caplets, capsules, satchet, and liquids (e.g., flavored syrups). Such dosage forms contain predetermined amounts of active ingredients and can be prepared by methods of pharmacy well known to those skilled in the art. See generally, *Remington's Pharmaceutical Sciences*, 20th ed., Mack Publishing, Easton Pa. (2000).

Typical oral dosage forms provided herein are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, micro-crystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms provided herein include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include the materials sold as AVICEL-PH-101, AVICEL-PH-103 AVICEL RC-581, AVICEL-PH-105 (available from FMC Corporation, American Viscose Division, Avicel Sales, Marcus Hook, Pa.) and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions is typically present in from about 50 to about 99 weight percent of the pharmaceutical composition or dosage form.

Disintegrants may be used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms provided herein include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms provided herein include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB—O—SIL (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

In one embodiment, a solid oral dosage form provided herein comprises either one of Compound A, Compound A1, Compound B, Compound B1, or Compound C, and anhydrous lactose, microcrystalline cellulose, polyvinylpyrrolidone, stearic acid, colloidal anhydrous silica and gelatin.

4.6.2 Delayed Release Dosage Forms

Active ingredients can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients provided herein. Thus, in some embodiments, provided herein are single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

4.6.3 Parenteral Dosage Forms

Parenteral dosage forms can be administered to patients by various routes including, but not limited to, subcutaneous, intravenous (including bolus injection), intramuscular and intraarterial. Because their administration typically bypasses patients' natural defenses against contaminants, parenteral dosage forms are preferably sterile or capable of being sterilized prior to administration to a patient. Non-limiting examples of parenteral dosage forms include solutions ready for injection, dry products ready to be dissolved or suspended in a pharmaceutically acceptable vehicle for injection, suspensions ready for injection and emulsions.

Suitable vehicles that can be used to provide parenteral dosage forms are well known to those skilled in the art. Non-limiting examples of suitable vehicles include Water for Injection USP; aqueous vehicles such as, but not limited to, Sodium Chloride Injection, Ringer's Injection, Dextrose Injection, Dextrose and Sodium Chloride Injection and Lactated Ringer's Injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate and benzyl benzoate.

Compounds that increase the solubility of one or more of the active ingredients disclosed herein can also be incorporated into the parenteral dosage forms provided herein. For example, cyclodextrin and its derivatives can be used to increase the solubility of either one of (S)—N-(2-(1-(3-ethoxy-4-methoxyphenyl)-2-(methylsulfonyl)ethyl)-1,3-dioxoisoindolin-4-yl)acetamide or (S)—N-(2-(1-(3-ethoxy-4-methoxyphenyl)-2-(methylsulfonyl)ethyl)-3-oxoisoindolin-4-yl)cyclopropanecarboxamide and their derivatives.

4.6.4 Topical and Mucosal Dosage Forms

Drugs can be applied locally to the skin and its adnexa or to a variety of mucous membranes. The routes that can be used include nasal, sublingual, vaginal, cystic, rectal, preputial, ocular, buccal or aural. Many dosage forms have been developed to deliver active principles to the site of application to produce local effects. Non-limiting examples of topical and mucosal dosage forms provided herein include sprays, inhalers, aerosols, ointments, creams, gels, pastes, dusting powders, lotions, liniments, poultices, solutions, emulsions, suspensions, eye drops or other ophthalmic preparations or other forms known to one of skill in the art. See, e.g., *Remington's Pharmaceutical Sciences*, 20th ed., Mack Publishing, Easton Pa. (2000); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms are well known to those skilled in the pharmaceutical arts and depend on the particular tissue to which a given pharmaceutical composition or dosage form will be applied. Non-limiting examples of typical excipients include water, acetone, ethanol, ethylene glycol, propylene glycol, butane-1,3-diol, isopropyl myristate, isopropyl palmitate, mineral oil and mixtures thereof to form solutions, emulsions or gels, which are non-toxic and pharmaceutically acceptable.

Moisturizers such as occlusives, humectants, emollients and protein rejuvenators can also be added to pharmaceutical compositions and dosage forms if desired. Examples of such additional ingredients are well known in the art. See, e.g., *Remington's Pharmaceutical Sciences*, 20th ed., Mack Publishing, Easton Pa. (2000).

Occlusives are substances that physically block water loss in the stratum corneum. Non-limiting examples of occlusives include petrolatum, lanolin, mineral oil, silicones such as dimethicone, zinc oxide and combinations thereof. Preferably, the occlusives are petrolatum and lanolin, more preferably petrolatum in a minimum concentration of 5%.

Humectants are substances that attract water when applied to the skin and theoretically improve hydration of the stratum corneum. However, the water that is drawn to the skin is water from other cells, not atmospheric water. With this type of moisturizer, evaporation from the skin can continue and actually can make the dryness worse. Non-limiting examples of humectants include glycerin, sorbitol, urea, alpha hydroxy acids, sugars and combinations thereof. Preferably, the humectants are alpha hydroxy acids, such as glycolic acid, lactic acid, malic acid, citric acid and tartaric acid.

Emollients are substances that smooth skin by filling spaces between skin flakes with droplets of oil, and are not usually occlusive unless applied heavily. When combined with an emulsifier, they may help hold oil and water in the stratum corneum. Vitamin E is a common additive, which appears to have no effect, except as an emollient. Likewise, other vitamins, for example, A and D, are also added, but their effect is questionable. Non-limiting examples of emollients include mineral oil, lanolin, fatty acids, cholesterol, squalene, structural lipids and combinations thereof.

Protein rejuvenators are substances that rejuvenate the skin by replenishing essential proteins. Non-limiting examples of protein rejuvenators include collagen, keratin, elastin and combinations thereof.

The pH of a pharmaceutical composition or dosage form may also be adjusted to improve delivery of one or more active ingredients. Similarly, the polarity of a solvent carrier, its ionic strength or tonicity can be adjusted to improve delivery. For example, absorption through the skin can also be enhanced by occlusive dressings, inunction or the use of dimethyl sulfoxide as a carrier. Compounds such as metal stearates (e.g., calcium stearate, zinc stearate, magnesium stearate, sodium stearate, lithium stearate, potassium stearate, etc.) can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant and as a delivery-enhancing or penetration-enhancing agent. Different salts, hydrates or solvates of the active ingredients can be used to further adjust the properties of the resulting composition.

In certain embodiments, one or both of the active agents as provided herein are administered parenterally, transdermally, mucosally, nasally, buccally, sublingualy, topically, or orally. In certain embodiments, the first active agent is administered orally in a tablet or capsule form. In certain embodiments, one or more of the active agents are administered topically (e.g. in the dosage form of a lotion or a liquid).

In certain embodiments, the composition provided herein may be applied in the form of a shampoo, foaming baths, spray, spot on, lotion, gels, emulsion, or other forms of application known to the person skilled in the art may also be used. A spray will mostly be used in curative application, whereas a shampoo mostly will have a cleaning and preventive function and a lotion is especially suitable for cleaning of exsudative lesions and ensures a major antiseptic action without distorting the microflora of the fur.

In certain embodiments, the compositions intended for pets, particularly cats and dogs, are generally applied by deposition on the skin ("spot on" or "pour on" application). This is generally a localized application to a region with a surface area of less than 10 cm², especially between 5 and 10 cm², in particular at two points and preferably localized between the animal's shoulders. After deposition, the composition diffuses, in particular over the animal's entire body, and then dries, without crystallizing or changing the appearance (in particular absence of any whitish deposit or of any dusty appearance) or the feel of the coat.

4.6.5 Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving the active ingredient, or a pharmaceutically acceptable salt, solvate, hydrate or prodrug thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the active ingredient. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, 5-35 mg or about 9-30 mg of lyophilized powder, is added per mL of sterile water or other suitable carrier. The precise amount depends upon the compound used. Such amount can be empirically determined.

In one embodiment, stereomerically pure apremilast, (+)-2-[1-(3-ethoxy-4-methoxyphenyl)-2-methylsulfonylethyl]-4-acetylaminoisoindoline-1,3-dione (Compound A1), is administered to the patient as described herein. In one embodiment, stereomerically pure apremilast, (+)-2-[1-(3-ethoxy-4-methoxyphenyl)-2-methylsulfonylethyl]-4-acetylaminoisoindoline-1,3-dione is provided for use in methods described herein.

In one embodiment, the dosage of apremilast, (+)-2-[1-(3-ethoxy-4-methoxyphenyl)-2-methylsulfonylethyl]-4-acetylaminoisoindoline-1,3-dione may be reduced to 30 mg once daily. In one embodiment, the dosage of apremilast, (+)-2-[1-(3-ethoxy-4-methoxyphenyl)-2-methylsulfonylethyl]-4-acetylaminoisoindoline-1,3-dione may be 30 mg twice daily. In one embodiment, the dosage of apremilast, (+)-2-[1-(3-ethoxy-4-methoxyphenyl)-2-methylsulfonylethyl]-4-acetylaminoisoindoline-1,3-dione can be increased to 60 mg per day, where the patient is optionally administered the 60 mg amount in two daily dosages.

In one embodiment, apremilast, (+)-2-[1-(3-ethoxy-4-methoxyphenyl)-2-methylsulfonylethyl]-4-acetylaminoisoindoline-1,3-dione, can be administered without regard to meals.

In some embodiments, the stereomerically pure (+)-2-[1-(3-ethoxy-4-methoxyphenyl)-2-methylsulfonylethyl]-4-acetylaminoisoindoline-1,3-dione comprises greater than about 90% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 95% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 96% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 97% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 98% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 99% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione is administered in an amount of about 20 mg twice a day.

In some embodiments, the stereomerically pure (+)-2-[1-(3-ethoxy-4-methoxyphenyl)-2-methylsulfonylethyl]-4-acetylaminoisoindoline-1,3-dione is administered in an amount of about 30 mg twice a day.

In some embodiments, the stereomerically pure (+)-2-[1-(3-ethoxy-4-methoxyphenyl)-2-methylsulfonylethyl]-4-acetylaminoisoindoline-1,3-dione is administered once or twice daily.

In some embodiments, the stereomerically pure (+)-2-[1-(3-ethoxy-4-methoxyphenyl)-2-methylsulfonylethyl]-4-acetylaminoisoindoline-1,3-dione is administered in tablet form. In some embodiments, the tablet comprises a 10 mg, 20 mg or 30 mg dose of stereomerically pure (+)-2-[1-(3-ethoxy-4-methoxyphenyl)-2-methylsulfonylethyl]-4-acetylaminoisoindoline-1,3-dione.

4.6.6 Kits

Active ingredients are often not administered to a patient at the same time or by the same route of administration. In some embodiments, provided herein are kits which, when used by the medical practitioner, can simplify the administration of appropriate amounts of active ingredients to a patient.

A typical kit comprises a unit dosage form of one of Compound A, Compound A1, Compound B, Compound B1, Compound C, or a pharmaceutically acceptable salt, stereoisomer, solvate, hydrate, clathrate, polymorph or prodrug thereof. In one embodiment, the kit further comprises a unit dosage form of a second active ingredient.

Kits can further comprise devices that are used to administer the active ingredient(s). Examples of such devices include, but are not limited to, syringes, drip bags, patches, and inhalers.

Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.7 Assays

Compounds having PDE4 inhibitory activity can be assayed using methods commonly known in the art including, but not limited to, enzyme immunoassay, radioimmunoassay, immunoelectrophoresis, and affinity labeling. Further assays which can be utilized include LPS-induced TNF and PDE4 enzymatic assays and the methods set out in International Patent Publication Nos. WO 01/90076 A1 WO 01/34606 A1 each of which are incorporated herein in their entireties by reference.

PBMC from normal donors are obtained by Ficoll-Hypaque density centrifugation. Cells are cultured in RPMI supplemented with 10%, AB+ serum, 2 mM L-glutamine, 100 U/mL penicillin and 100 mg/mL streptomycin.

The test compounds are dissolved in dimethylsulfoxide (Sigma Chemical), further dilutions are done in supplemented RPMI. The final dimethylsulfoxide concentration in the presence or absence of drug in the PBMC suspensions is 0.25 wt %. The test compounds are assayed at half-log dilutions starting in 50 mg/mL. The test compounds are added to PBMC ($10^6$ cells/mL) in 96 wells plates one hour before the addition of LPS.

PBMC ($10^6$ cells/mL) in the presence or absence of test compounds are stimulated by treatment with 1 mg/mL of LPS from *Salmonella minnesota* R595 (List Biological Labs, Campbell, Calif.). Cells are then incubated at 37° C. for 18-20 hours. Supernatants are harvested and assayed immediately for TNFα levels or kept frozen at −70° C. (for not more than 4 days) until assayed.

The concentration of TNFα in the supernatant is determined by human TNFα ELISA kits (ENDOGEN, Boston, Mass.) according to the manufacturer's directions.

Phosphodiesterase can be determined in conventional models. For example, using the method of Hill and Mitchell, U937 cells of the human promonocytic cell line are grown to $1×10^6$ cells/mL and collected by centrifugation. A cell pellet of $1×10^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N',N'-tetraacetic acid (EGTA), 1 µM phenyl-methylsulfonyl fluoride (PMSF), and 1 µg/mL leupeptin). Cells are homogenized with 20 strokes in a Dounce homogenizer and supernatant containing the cytosolic fraction are obtained by centrifugation. The supernatant then is loaded onto a Sephacryl S-200 column equilibrated in homogenization buffer. Phosphodiesterase is eluted in homogenization buffer at a rate of approximately 0.5 mL/min and fractions are assayed for phosphodiesterase activity −/+ rolipram. Fractions containing phosphodiesterase activity (rolipram sensitive) are pooled and aliquoted for later use.

The phosphodiesterase assay is carried out in a total volume of 100 µl containing various concentration of test compounds, 50 mM Tris-HCl, pH 7.5, 5 mM magnesium chloride, and 1 µM cAMP of which 1% was $^3$H cAMP. Reactions are incubated at 30° C. for 30 minutes and terminated by boiling for 2 minutes. The amount of phosphodiesterase IV containing extract used for these experiments is predetermined such that reactions are within the linear range and consumed less than 15% of the total substrate. Following termination of reaction, samples are chilled at 4° C. and then treated with 10 µl 10 mg/mL snake venom for 15 min at 30° C. Unused substrate then is removed by adding 200 µl of a quaternary ammonium ion exchange resin (AG1-X8, BioRad) for 15 minutes. Samples then are spun at 3000 rpm, 5 min and 50 µl of the aqueous phase are taken for counting. Each data point is carried out in duplicate and activity is expressed as percentage of control. The $IC_{50}$ of the compound then is determined from dose response curves of a minimum of three independent experiments.

4.7.1 Induction of IL-4 and IL-10 Release

IL-4, among others, serves as a growth and differentiation factor for B cells, mast cells and macrophages and thus, may play a role in cell mediated immunity. In addition, IL-10, which inhibits cytokine synthesis by $T_H1$ cells, may be therapeutically effective in suppressing T lymphocyte autoimmunity.

To assess whether a PDE4 modulator provided herein can induce the release of IL-4 and IL-10, a PDE4 modulator and/or vehicle are incubated with human PBML. Concanavalin A is then added to stimulate the cells overnight at 37° C. IL-4 and IL-10 levels in the conditioned medium are quantified using any methods known in the art, for example, a sandwich ELISA.

4.7.2 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 g/ml streptomycin (Life Technologies).

PBMC ($2×10^5$ cells) are plated in 96-well flat-bottom Costar tissue culture plates (Corning, N.Y., USA) in triplicate. Cells are stimulated with LPS (from *Salmonella abortus equi*, Sigma cat. no. L-1887, St. Louis, Mo., USA) at 1 ng/ml final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNF levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

The embodiments described above are intended to be merely exemplary, and those skilled in the art will recognize, or will be able to ascertain using no more than routine experimentation, numerous equivalents of specific compounds, materials, and procedures. All such equivalents are

What is claimed:

1. A method of treating, preventing, or managing immune reconstitution inflammatory syndrome (IRIS) in a subject in need thereof, said method comprising administering to said subject an effective amount of a PDE4 modulator, wherein the PDE4 modulator is (A)

[chemical structure A]

(B)

[chemical structure B]

, or (C)

[chemical structure C]

or an enantiomer, mixture of enantiomers, or a pharmaceutically acceptable salt thereof.

2. The method of claim 1, wherein said patient is a HIV patient.

3. A method of preventing IRIS in a HIV patient prior to administration of antiretroviral therapy (ART) or prior to withdrawal of ART, said method comprising administering to said patient an effective amount of a PDE4 modulator.

4. A method of treating or reducing IRIS in a HIV patient after administration of ART or after withdrawal of ART, said method comprising administering to said patient an effective amount of a PDE4 modulator.

5. The method of claim 1, wherein said PDE4 modulator is

[chemical structure]

or an enantiomer, mixture of enantiomers, or a pharmaceutically acceptable salt thereof.

6. The method of claim 1, wherein said PDE4 modulator is

[chemical structure]

or an enantiomer, mixture of enantiomers, or a pharmaceutically acceptable salt thereof.

7. The method of claim 1, wherein said PDE4 modulator is

[chemical structure]

or an enantiomer, mixture of enantiomers, or a pharmaceutically acceptable salt thereof.

8. The method of claim 1, wherein said PDE4 modulator is administered orally to said patient.

9. The method of claim 8, wherein said PDE4 modulator is administered in a tablet, capsule, or sachet form.

10. The method of claim 1, wherein said PDE4 modulator is a component of a pharmaceutical composition.

11. The method of claim 1, wherein said PDE4 modulator is administered in combination with a second active agent.

12. The method of claim 11, wherein said second active agent is a non-steroidal anti-inflammatory drug, a corticosteroid, an antimicrobial agent, an anti-fungal agent, or an anti-tuberculosis agent.

13. The method of claim 1, wherein said PDE4 modulator inhibits production or signaling of one or more cytokines selected from the group consisting of TNF-α, IL-12, MIP-1α, MCP-1, IP-10, IFN-γ, MIG, GM-CSF, IL-1β, RANTES, and IL-8.

14. The method of claim 1, wherein said patient is a patient at risk of developing IRIS.

15. The method of claim 14, wherein said patient is an HIV patient at risk of developing IRIS and is administered said PDE4 modulator before administration of antiretroviral therapy (ART).

16. The method of claim 1, wherein said patient presents or has developed IRIS.

17. The method of claim 16, wherein said patient is an HIV patient presenting or having developed IRIS and is administered said PDE4 modulator after initiation or re-initiation of ART.

18. The method of claim 1, wherein said IRIS is characterized by or results from an opportunistic bacterial infection.

19. The method of claim 1, wherein said IRIS is characterized by or results from an opportunistic fungal infection.

20. The method of claim 1, wherein said IRIS is characterized by or results from an opportunistic parasitic infection.

21. The method of claim 1, wherein said IRIS is characterized by or results from cytomegalovirus (CMV), CMV retinitis, crytoccocal meningitis, croyptococcosis, eosinophilic folliculitis, hepatitis B, hepatitis C, herpes virus, herpes simplex virus (HSV), varicella zoster virus (shingles), human pampillomavirus (HPV), karposi sarcoma (HHV8), *Mycobacterium avium* complex (MAC), *Pneumocystis jiroveci* pneumonia (PCP), progressive multifocal leukoencephalopathy (PML), or *Mycobacterium tuberculosis* (TB).

22. The method of claim 1, wherein said patient has a decreased CD4+ count compared to a non-immunodeficient subject.

23. The method of claim 1, wherein said patient has a decreased HIV titer of at least 0.5 $\log_{10}$ following administration of ART.

* * * * *